United States Patent
Boyle et al.

(10) Patent No.: US 8,677,995 B2
(45) Date of Patent: *Mar. 25, 2014

(54) COMPRESSOR CONTROL SYSTEM FOR A PORTABLE VENTILATOR

(75) Inventors: David Boyle, Monrovia, CA (US);
Michael Holmes, Redlands, CA (US);
Malcolm Williams, San Clemente, CA (US)

(73) Assignee: CareFusion 203, Inc., San Diego, CA (US)

( * ) Notice: Subject to any disclaimer, the term of this patent is extended or adjusted under 35 U.S.C. 154(b) by 733 days.

This patent is subject to a terminal disclaimer.

(21) Appl. No.: 11/877,117

(22) Filed: Oct. 23, 2007

(65) Prior Publication Data

US 2008/0092892 A1 Apr. 24, 2008

Related U.S. Application Data

(63) Continuation of application No. 10/847,693, filed on May 18, 2004, now Pat. No. 7,607,437.

(60) Provisional application No. 60/492,421, filed on Aug. 4, 2003.

(51) Int. Cl.
*A61M 16/00* (2006.01)
*H02P 5/00* (2006.01)

(52) U.S. Cl.
USPC ............ 128/204.21; 128/200.24; 128/204.18

(58) Field of Classification Search
USPC ............ 128/200.24, 204.18, 204.21, 204.19;
318/808, 400.14, 400.11, 400.01,
318/400.04, 400.09, 400.15, 400.17,
318/400.22, 400.37, 400.38; 73/1.41;
388/800, 809, 803, 806; 700/282

See application file for complete search history.

(56) References Cited

U.S. PATENT DOCUMENTS

| 56,611 A | 7/1866 | Reynold |
| 56,614 A | 7/1866 | Roots et al. |

(Continued)

FOREIGN PATENT DOCUMENTS

| DE | 3238015 | 4/1984 |
| DE | 3414064 | 10/1985 |

(Continued)

OTHER PUBLICATIONS

Hinrichs, Dr. Gustavus. Introduction to General Chemistry, a Graded Course of One Hundred Lectures. St. Louis, MO: Hinrichs, 1897. pp. 87-89.*

(Continued)

*Primary Examiner* — Annette Dixon
(74) *Attorney, Agent, or Firm* — McDermott Will & Emery LLP

(57) ABSTRACT

A method and apparatus for controlling a brushless DC (BLDC) motor over a wide range of angular speeds is presented. Analog magnetic sensors provide continuous signal measurements related to the rotor angular position at a sample rate independent of rotor angular speed. In one embodiment, analog signal measurements are subsequently processed using an arctangent function to obtain the rotor angular position. The arctangent may be computed using arithmetic computation, a small angle approximation, a polynomial evaluation approach, a table lookup approach, or a combination of various methods. In one embodiment, the BLDC rotor is used to drive a Roots blower used as a compressor in a portable mechanical ventilator system.

22 Claims, 12 Drawing Sheets

(56) References Cited

U.S. PATENT DOCUMENTS

| | | | |
|---|---|---|---|
| 587,907 A | 8/1897 | Ames et al. | |
| 1,769,153 A | 7/1930 | Meyer | |
| 2,014,932 A | 9/1935 | Hallett | 230/141 |
| 2,787,999 A | 4/1957 | Bennett | 128/30 |
| 3,089,638 A | 5/1963 | Rose | 230/141 |
| 3,094,274 A | 6/1963 | Thompson | 230/224 |
| 3,371,856 A | 3/1968 | Thelen et al. | 230/141 |
| 3,459,395 A | 8/1969 | Scotto | 248/20 |
| 3,658,443 A | 4/1972 | Fumagalli | 417/394 |
| 3,865,523 A | 2/1975 | Baehr | |
| 3,905,362 A | 9/1975 | Eyrick et al. | |
| 3,916,888 A | 11/1975 | Buck et al. | |
| 3,941,206 A | 3/1976 | Halter | 181/50 |
| 4,080,103 A | 3/1978 | Bird | 417/3 |
| 4,096,858 A | 6/1978 | Eyrick et al. | |
| 4,121,578 A | 10/1978 | Torzala | 128/142 R |
| 4,182,599 A | 1/1980 | Eyrick et al. | |
| 4,215,977 A | 8/1980 | Weatherston | 418/1 |
| 4,220,219 A | 9/1980 | Flugger | 181/265 |
| 4,227,869 A | 10/1980 | Eriksson | 418/206 |
| 4,239,039 A | 12/1980 | Thompson | 128/205.24 |
| 4,248,194 A | 2/1981 | Drutchas et al. | |
| 4,257,453 A | 3/1981 | Kohnke | |
| 4,267,899 A | 5/1981 | Wagner et al. | 181/272 |
| 4,323,064 A | 4/1982 | Hoenig et al. | 128/204.21 |
| 4,448,192 A | 5/1984 | Stawitcke et al. | 128/204.26 |
| 4,455,132 A | 6/1984 | Messori | 418/206 |
| 4,495,947 A | 1/1985 | Motycha | 128/205.14 |
| 4,564,345 A | 1/1986 | Mueller | 418/206 |
| 4,595,349 A | 6/1986 | Preston et al. | 418/206 |
| 4,609,335 A | 9/1986 | Uthoff, Jr. | 418/201 |
| 4,637,439 A | 1/1987 | Jeans | |
| 4,656,553 A | 4/1987 | Brown | |
| 4,666,384 A | 5/1987 | Kaga et al. | 418/150 |
| 4,673,058 A | 6/1987 | Roberts et al. | 181/266 |
| 4,684,330 A | 8/1987 | Andersson et al. | 417/360 |
| 4,686,999 A | 8/1987 | Snyder et al. | |
| 4,702,240 A | 10/1987 | Chaoui | 128/204.18 |
| 4,747,403 A | 5/1988 | Gluck et al. | |
| 4,768,934 A | 9/1988 | Soeters, Jr. | 418/1 |
| 4,781,541 A | 11/1988 | Sohler et al. | 417/312 |
| 4,794,922 A | 1/1989 | DeVries | 128/204.18 |
| 4,838,257 A | 6/1989 | Hatch | |
| 4,844,044 A | 7/1989 | McGovern | 123/559.1 |
| 4,846,302 A | 7/1989 | Hetherington | 181/243 |
| 4,867,151 A | 9/1989 | Bird | 128/201.17 |
| 4,897,583 A * | 1/1990 | Rees | 318/400.13 |
| 4,905,685 A | 3/1990 | Olsson et al. | |
| 4,938,670 A | 7/1990 | Lee | 418/150 |
| 4,957,107 A | 9/1990 | Sipin | 128/204.21 |
| 4,975,032 A | 12/1990 | Arai et al. | 418/150 |
| 5,040,959 A | 8/1991 | Fukagawa | 418/150 |
| 5,056,995 A | 10/1991 | Tamura et al. | 418/201.1 |
| 5,127,400 A | 7/1992 | DeVries et al. | |
| 5,131,829 A | 7/1992 | Hampton | 418/189 |
| 5,145,349 A | 9/1992 | McBurnett | 418/206 |
| 5,152,684 A | 10/1992 | Steffens | 418/150 |
| 5,161,525 A | 11/1992 | Kimm et al. | 128/204.26 |
| 5,211,170 A | 5/1993 | Press | 128/204.18 |
| 5,222,148 A | 6/1993 | Yuan | |
| 5,237,987 A | 8/1993 | Anderson et al. | 128/204.18 |
| 5,239,994 A | 8/1993 | Atkins | 128/204.18 |
| 5,253,486 A | 10/1993 | Sugahara et al. | |
| 5,335,651 A | 8/1994 | Foster et al. | |
| 5,350,888 A | 9/1994 | Sager, Jr. et al. | 181/247 |
| 5,384,527 A * | 1/1995 | Rozman et al. | 322/10 |
| 5,388,575 A | 2/1995 | Taube | |
| 5,398,676 A | 3/1995 | Press et al. | |
| 5,428,276 A * | 6/1995 | Carobolante et al. | 318/400.14 |
| 5,430,362 A * | 7/1995 | Carr et al. | 318/779 |
| 5,439,358 A | 8/1995 | Weinbrecht | |
| 5,452,714 A | 9/1995 | Anderson et al. | |
| 5,461,293 A * | 10/1995 | Rozman et al. | 318/603 |
| 5,493,200 A * | 2/1996 | Rozman et al. | 322/10 |
| 5,493,892 A | 2/1996 | Sherman | |
| 5,495,162 A * | 2/1996 | Rozman et al. | 322/10 |
| 5,495,163 A * | 2/1996 | Rozman et al. | 322/10 |
| 5,542,416 A | 8/1996 | Chalvignac | 128/204.23 |
| 5,577,152 A | 11/1996 | Chen | 388/804 |
| 5,582,163 A | 12/1996 | Bonassa | 128/204.26 |
| 5,632,270 A | 5/1997 | O'Mahony et al. | 128/204.24 |
| 5,638,600 A | 6/1997 | Rao et al. | 29/888.02 |
| 5,664,563 A | 9/1997 | Schroeder et al. | |
| 5,687,717 A | 11/1997 | Halpern et al. | 128/630 |
| 5,694,926 A | 12/1997 | DeVries et al. | |
| 5,701,883 A | 12/1997 | Hete et al. | 128/204.26 |
| 5,702,240 A | 12/1997 | O'Neal et al. | 418/9 |
| 5,720,276 A | 2/1998 | Kobatake et al. | |
| 5,760,348 A | 6/1998 | Heuser | 181/272 |
| 5,763,792 A | 6/1998 | Kullik | 73/861.53 |
| 5,783,782 A | 7/1998 | Sterrett et al. | 181/272 |
| 5,799,652 A | 9/1998 | Kotliar | |
| 5,823,186 A | 10/1998 | Rossen et al. | 128/204.21 |
| 5,831,223 A | 11/1998 | Kesselring | 181/227 |
| 5,868,133 A | 2/1999 | DeVries et al. | 128/204.21 |
| 5,871,465 A | 2/1999 | Vasko | |
| 5,880,586 A | 3/1999 | Dukart et al. | |
| 5,881,722 A | 3/1999 | DeVries et al. | 128/204.21 |
| 5,918,597 A | 7/1999 | Jones et al. | |
| 5,931,159 A | 8/1999 | Suzuki et al. | 128/204.18 |
| 5,934,274 A | 8/1999 | Merrick et al. | |
| 5,944,501 A | 8/1999 | Yokoi | 418/181 |
| 5,996,731 A | 12/1999 | Czabala et al. | |
| 6,009,871 A | 1/2000 | Kiske et al. | 128/204.21 |
| 6,065,944 A | 5/2000 | Cobb | |
| 6,070,576 A | 6/2000 | Banucci et al. | |
| 6,076,523 A | 6/2000 | Jones et al. | |
| 6,099,277 A | 8/2000 | Patel et al. | 418/1 |
| 6,102,038 A | 8/2000 | DeVries | 128/205.24 |
| 6,125,844 A | 10/2000 | Samiotes | 128/200.23 |
| 6,152,129 A | 11/2000 | Berthon-Jones | |
| 6,152,135 A | 11/2000 | DeVries et al. | 128/205.24 |
| 6,155,257 A | 12/2000 | Lurie et al. | 128/204.23 |
| 6,158,430 A | 12/2000 | Pfeiffer et al. | |
| 6,158,434 A | 12/2000 | Lugtigheid et al. | 128/204.22 |
| 6,164,412 A | 12/2000 | Allman | 181/272 |
| 6,176,693 B1 | 1/2001 | Conti | |
| 6,237,592 B1 * | 5/2001 | Surjadi et al. | 128/204.21 |
| 6,239,564 B1 | 5/2001 | Boe et al. | |
| 6,247,906 B1 | 6/2001 | Pijanowski | |
| 6,279,574 B1 | 8/2001 | Richardson et al. | 128/204.18 |
| 6,279,576 B1 | 8/2001 | Lambert | |
| 6,283,246 B1 | 9/2001 | Nishikawa | 181/255 |
| 6,305,372 B1 | 10/2001 | Servidio | 128/204.21 |
| 6,349,724 B1 | 2/2002 | Burton et al. | |
| 6,354,558 B1 | 3/2002 | Li | 248/615 |
| 6,412,483 B1 | 7/2002 | Jones et al. | |
| 6,468,222 B1 | 10/2002 | Mault et al. | |
| 6,474,960 B1 | 11/2002 | Hansman | 417/363 |
| 6,479,987 B1 | 11/2002 | Marx et al. | |
| 6,484,719 B1 | 11/2002 | Berthon-Jones | |
| 6,526,970 B2 | 3/2003 | DeVries et al. | |
| 6,543,449 B1 | 4/2003 | Woodring et al. | 128/204.18 |
| 6,558,137 B2 | 5/2003 | Tomell et al. | |
| 6,564,798 B1 | 5/2003 | Jalde | 128/205.24 |
| 6,571,792 B1 | 6/2003 | Hendrickson et al. | 128/203.12 |
| 6,571,796 B2 | 6/2003 | Banner et al. | 128/204.26 |
| 6,591,835 B1 | 7/2003 | Blanch | 128/204.25 |
| 6,615,446 B2 | 9/2003 | Noreen et al. | |
| 6,615,831 B1 | 9/2003 | Tuitt et al. | 128/204.18 |
| 6,619,286 B2 | 9/2003 | Patel | 128/204.26 |
| 6,619,325 B2 | 9/2003 | Gray, Jr. | |
| 6,626,175 B2 | 9/2003 | Jafari et al. | 128/204.21 |
| 6,629,525 B2 | 10/2003 | Hill et al. | 128/202.26 |
| 6,629,531 B2 | 10/2003 | Gleason et al. | 128/205.25 |
| 6,629,934 B2 | 10/2003 | Mault et al. | 600/538 |
| 6,631,716 B1 | 10/2003 | Robinson et al. | 128/204.21 |
| 6,637,430 B1 | 10/2003 | Voges et al. | 128/200.14 |
| 6,651,658 B1 | 11/2003 | Hill et al. | |
| 6,666,209 B2 | 12/2003 | Bennett et al. | 128/200.24 |
| 6,672,300 B1 | 1/2004 | Grant | 124/204.26 |
| 6,691,702 B2 | 2/2004 | Appel et al. | 128/202.26 |
| 6,691,707 B1 | 2/2004 | Gunaratnam et al. | 128/206.21 |
| 6,708,690 B1 | 3/2004 | Hete et al. | 128/204.18 |

(56) References Cited

U.S. PATENT DOCUMENTS

| | | | |
|---|---|---|---|
| 6,745,770 B2 | 6/2004 | McAuliffe et al. | 128/205.24 |
| 6,752,240 B1 | 6/2004 | Schlagenhaft | 181/249 |
| 6,764,534 B2 | 7/2004 | McCombs et al. | 96/111 |
| 6,770,037 B2 | 8/2004 | Sullivan et al. | 600/529 |
| 6,782,888 B1 | 8/2004 | Friberg et al. | 128/204.18 |
| 6,802,225 B2 | 10/2004 | Shahar et al. | 73/861.52 |
| 6,820,618 B2 | 11/2004 | Banner et al. | 128/204.23 |
| 6,837,239 B2 | 1/2005 | Beizndtsson et al. | |
| 6,837,260 B1 | 1/2005 | Kuehn | 137/315.01 |
| 6,877,511 B2 | 4/2005 | DeVries et al. | |
| 6,907,373 B2 | 6/2005 | Walter et al. | |
| 6,968,842 B1 | 11/2005 | Truschel et al. | 128/204.18 |
| 6,979,181 B1 * | 12/2005 | Kidd | 318/400.08 |
| 7,004,908 B2 | 2/2006 | Sullivan et al. | 600/529 |
| 7,011,092 B2 | 3/2006 | McCombs et al. | 128/205.12 |
| 7,032,589 B2 | 4/2006 | Kerechanin et al. | 128/200.24 |
| 7,063,084 B2 | 6/2006 | McDonald | 128/200.28 |
| 7,066,178 B2 | 6/2006 | Gunaratnam et al. | 128/206.21 |
| 7,066,985 B2 | 6/2006 | Deane et al. | 95/96 |
| 7,073,499 B1 | 7/2006 | Reinhold et al. | 128/200.18 |
| 7,086,366 B1 | 8/2006 | Killion | 123/192.2 |
| 7,118,536 B2 | 10/2006 | Haberland et al. | 600/538 |
| 7,121,276 B2 | 10/2006 | Jagger et al. | 128/201.21 |
| 7,168,429 B2 | 1/2007 | Matthews et al. | 128/204.21 |
| 7,171,963 B2 | 2/2007 | Jagger et al. | 128/201.21 |
| 7,183,681 B2 | 2/2007 | Segawa et al. | 310/68 B |
| 7,188,621 B2 | 3/2007 | DeVries | |
| 7,225,809 B1 | 6/2007 | Bowen et al. | |
| 7,226,280 B1 | 6/2007 | Yokoi | 418/206.4 |
| 7,329,304 B2 | 2/2008 | Bliss et al. | 95/12 |
| 7,331,342 B2 | 2/2008 | Spearman et al. | 128/203.14 |
| 7,335,243 B2 | 2/2008 | Homan et al. | 55/385.2 |
| 7,351,034 B2 | 4/2008 | Cens et al. | |
| 7,368,005 B2 | 5/2008 | Bliss et al. | 96/121 |
| 2001/0044588 A1 | 11/2001 | Mault | 600/549 |
| 2002/0134378 A1 | 9/2002 | Finnegan et al. | |
| 2003/0024529 A1 | 2/2003 | Beizndtsson et al. | |
| 2003/0057904 A1 | 3/2003 | Sacher | 318/268 |
| 2003/0208113 A1 | 11/2003 | Mault et al. | 600/316 |
| 2004/0015364 A1 | 1/2004 | Sulc | |
| 2004/0040563 A1 | 3/2004 | Chu et al. | |
| 2004/0061996 A1 | 4/2004 | Kamphuis et al. | |
| 2004/0074495 A1 | 4/2004 | Wickham et al. | |
| 2004/0147818 A1 | 7/2004 | Levy et al. | 600/300 |
| 2004/0190236 A1 | 9/2004 | Medica et al. | |
| 2004/0211422 A1 | 10/2004 | Arcilla et al. | 128/204.19 |
| 2004/0221854 A1 | 11/2004 | Hete et al. | |
| 2004/0226562 A1 | 11/2004 | Bordewick | 128/204.23 |
| 2005/0051168 A1 | 3/2005 | DeVries et al. | |
| 2005/0112013 A1 | 5/2005 | DeVries et al. | |
| 2005/0124866 A1 | 6/2005 | Elaz et al. | |
| 2005/0166921 A1 | 8/2005 | DeVries et al. | |
| 2005/0183902 A1 | 8/2005 | Segawa et al. | |
| 2005/0188991 A1 | 9/2005 | Sun et al. | 128/204.23 |
| 2005/0241642 A1 | 11/2005 | Krzysztofik | 128/206.15 |
| 2006/0065672 A1 | 3/2006 | Lecourt et al. | |
| 2006/0069326 A1 | 3/2006 | Heath | 601/41 |
| 2006/0070624 A1 | 4/2006 | Kane et al. | 128/204.23 |
| 2006/0124128 A1 | 6/2006 | Deane et al. | 128/204.21 |
| 2006/0144396 A1 | 7/2006 | DeVries et al. | |
| 2006/0144399 A1 | 7/2006 | Davidowski et al. | 128/205.21 |
| 2006/0144405 A1 | 7/2006 | Gunaratnam et al. | 128/206.21 |
| 2006/0150973 A1 | 7/2006 | Chalvignac | 128/214.21 |
| 2006/0174871 A1 | 8/2006 | Jagger et al. | 128/201.21 |
| 2006/0174872 A1 | 8/2006 | Jagger et al. | 128/201.21 |
| 2006/0174874 A1 | 8/2006 | Jagger et al. | 128/201.21 |
| 2006/0174875 A1 | 8/2006 | Jagger et al. | 128/201.21 |
| 2006/0174877 A1 | 8/2006 | Jagger et al. | 128/201.21 |
| 2006/0174878 A1 | 8/2006 | Jagger et al. | 128/201.21 |
| 2006/0174880 A1 | 8/2006 | Jagger et al. | 128/201.25 |
| 2006/0174881 A1 | 8/2006 | Jagger et al. | 128/201.25 |
| 2006/0174882 A1 | 8/2006 | Jagger et al. | 128/201.25 |
| 2006/0201503 A1 | 9/2006 | Breen | 128/204.18 |
| 2006/0213518 A1 | 9/2006 | DeVries et al. | |
| 2006/0249149 A1 | 11/2006 | Meier et al. | 128/204.18 |
| 2006/0266355 A1 | 11/2006 | Misholi | 128/204.23 |
| 2006/0283450 A1 | 12/2006 | Shissler et al. | 128/204.21 |
| 2007/0044799 A1 | 3/2007 | Hete et al. | 128/205.11 |
| 2007/0062529 A1 | 3/2007 | Choncholas et al. | 128/204.22 |
| 2007/0062532 A1 | 3/2007 | Choncholas | 128/204.23 |
| 2007/0068526 A1 | 3/2007 | Lang et al. | 128/204.22 |
| 2007/0079826 A1 | 4/2007 | Kramer et al. | 128/200.14 |
| 2007/0113843 A1 | 5/2007 | Hughes | 128/200.24 |
| 2007/0113849 A1 | 5/2007 | Matthews et al. | 128/204.22 |
| 2007/0169776 A1 | 7/2007 | Kepler et al. | 128/200.23 |
| 2007/0181127 A1 | 8/2007 | Jin et al. | 128/204.21 |
| 2007/0193580 A1 | 8/2007 | Feldhahn et al. | 128/204.18 |
| 2007/0215146 A1 | 9/2007 | Douglas et al. | 128/200.24 |
| 2007/0221224 A1 | 9/2007 | Pittman et al. | 128/204.22 |
| 2007/0235030 A1 | 10/2007 | Teetzel et al. | 128/205.12 |
| 2007/0265877 A1 | 11/2007 | Rice et al. | 705/2 |
| 2007/0277825 A1 | 12/2007 | Bordewick et al. | 128/204.23 |
| 2008/0000474 A1 | 1/2008 | Jochle et al. | 128/204.18 |
| 2008/0029096 A1 | 2/2008 | Kollmeyer et al. | 128/204.21 |
| 2008/0035149 A1 | 2/2008 | Sutton | 128/205.24 |
| 2008/0039701 A1 | 2/2008 | Ali et al. | 600/301 |
| 2008/0051674 A1 | 2/2008 | Davenport et al. | |
| 2008/0066739 A1 | 3/2008 | LeMahieu et al. | 128/200.14 |
| 2008/0078395 A1 | 4/2008 | Ho et al. | 128/205.24 |
| 2008/0099017 A1 | 5/2008 | Bordewick et al. | 128/204.21 |
| 2008/0110455 A1 | 5/2008 | Dunsmore et al. | 128/200.24 |
| 2008/0110458 A1 | 5/2008 | Srinivasan et al. | 128/203.26 |
| 2008/0110462 A1 | 5/2008 | Chekal et al. | 128/204.26 |
| 2008/0127976 A1 | 6/2008 | Acker et al. | 128/204.18 |

FOREIGN PATENT DOCUMENTS

| | | |
|---|---|---|
| DE | 3620792 | 12/1987 |
| DE | 19817356 | 10/1999 |
| EP | 0239026 | 9/1987 |
| EP | 0521709 | 1/1993 |
| EP | 0938969 | 9/1999 |
| EP | 1130761 | 9/2001 |
| EP | 1243282 | 9/2002 |
| FR | 2875891 | 9/2004 |
| FR | 20040452189 | 3/2006 |
| GB | 1387841 | 3/1975 |
| GB | 1447091 | 8/1976 |
| GB | 2157370 | 10/1985 |
| JP | 08-010331 | 1/1996 |
| JP | 2001050774 | 2/2001 |
| JP | 2003124986 | 4/2003 |
| WO | WO 89/10768 | 11/1989 |
| WO | WO 92/11054 | 7/1992 |
| WO | WO 96/11717 | 4/1996 |
| WO | WO 97/11522 | 3/1997 |
| WO | WO 97/15343 | 5/1997 |
| WO | WO 99/64825 | 12/1999 |
| WO | WO 00/45883 | 8/2000 |
| WO | WO 02/11861 | 2/2002 |
| WO | WO 2004/040745 | 5/2004 |
| WO | WO-2005/013879 | 2/2005 |

OTHER PUBLICATIONS

M.L. Munjal, "Acoustics of Ducts and Mufflers," John Wiley & Sons, 1987, chapter 8.

Eaton—Supercharger Division, "Why an Eaton Supercharger?", www.eaton/consupercharger/whysuper.html.

Office Action, CA Application No. 2,574,018, mailed May 9, 2012, 4 pages.

Extended European Search Report, EP Application No. 07809783.9, Mailed Jun. 6, 2012, 8 pages.

Office Action, JP Application No. 2009-519444, mailed Jan. 10, 2012, 3 pages.

* cited by examiner

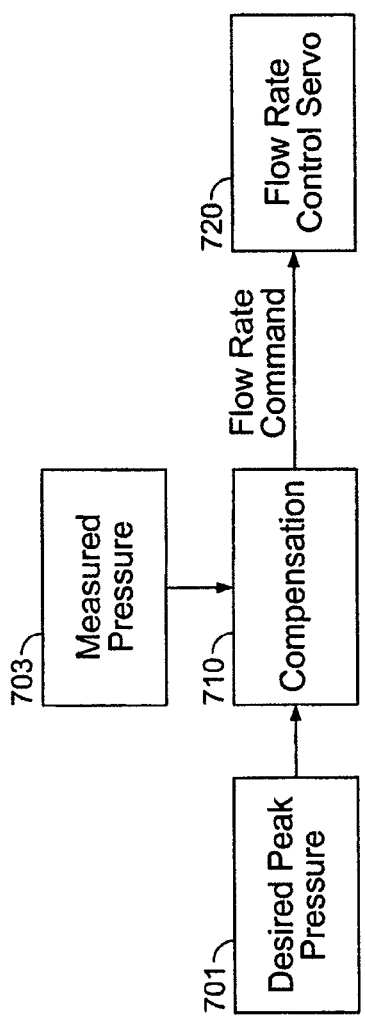
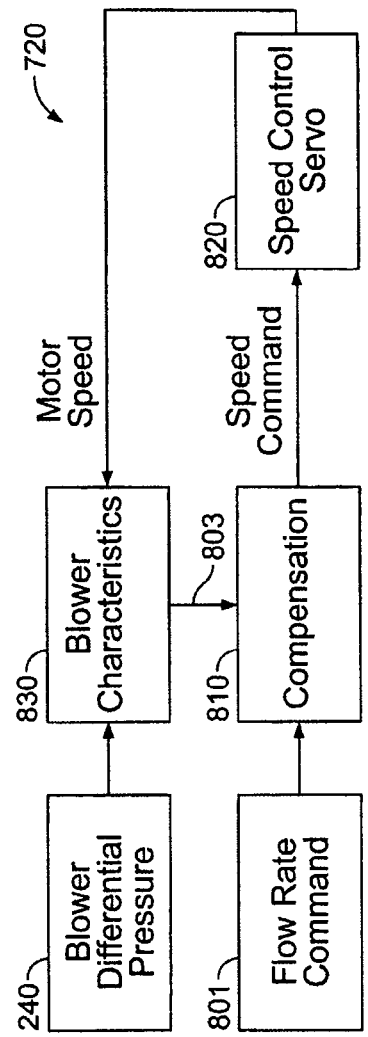
FIG. 7
FIG. 8

COMPRESSOR CONTROL SYSTEM FOR A PORTABLE VENTILATOR

CROSS-REFERENCE TO RELATED APPLICATIONS

This application claims priority to and is a continuation of U.S. patent application Ser. No. 10/847,693, titled "Compressor Control System for a Portable Ventilator," filed on May 18, 2004 now U.S. Pat. No. 7,607,437, which claims priority to U.S. Provisional Application No. 60/492,421, to Douglas F. DeVries, titled "Portable Ventilator," filed on Aug. 4, 2003, the disclosures of which are hereby incorporated by reference in their entirety.

BACKGROUND OF THE INVENTION

1. Field of the Invention

This invention relates to control systems for electric motors, more particularly to a control system for an electric motor used to drive a compressor in a portable ventilator.

2. Background Art

For a variety of reasons, there are instances when individuals (patients) with acute and chronic respiratory distress cannot ventilate themselves (i.e. breathe). In those circumstances, such patients require breathing assistance to stay alive. One solution is to provide those patients with a medical device called a mechanical ventilator, which assists with their breathing.

A purpose of a mechanical ventilator is to reproduce the body's normal breathing mechanism. Most mechanical ventilators create positive intrapulmonary pressure to assist breathing. Positive intrapulmonary pressure is created by delivering gas to the patient's lungs so that positive pressure is created within the alveoli (i.e. the final branches of the respiratory tree that act as the primary gas exchange units of the lung). Thus, a mechanical ventilator is essentially a device that generates a controlled flow of gas (e.g., air or oxygen) into a patient's airways during the inhalation phase, and allows gas to flow out of the lungs during the exhalation phase.

Mechanical ventilators use various types of methods to facilitate precise delivery of air to the patient. Some ventilators use gas compressors to generate the proper amount of flow to satisfy the requirements of the patient.

Most ventilator systems that have an internal gas source use either constant speed or variable speed compressors. Constant speed compressors are usually continuously operating, rotary-based machines that generate the desired flow from external air, for ultimate delivery to the patient. These constant speed systems generally use a downstream flow valve to control intermittent patient flow, with a bypass valve recirculating the excess flow.

Variable speed compressors operate by rapidly accelerating from a rest state to produce the flow rate necessary during the beginning of the inhalation cycle, and then decelerating to the rest state at the end of the inhalation cycle to allow the patient to exhale.

There are basically two types of variable speed systems employed in the mechanical ventilator art: piston-based systems and rotary-based systems. Rotary systems require low inertia components for the rapid acceleration and deceleration cycles. For instance, prior art systems, such as that described in U.S. Pat. No. 5,868,133 to DeVries et al, use drag compressors to provide the desired inspiratory air flow.

Rotary compressor systems deliver the required air flow during inhalation by accelerating the compression rotor(s) to the desired speed at the beginning of each inspiratory phase and decelerating the compression rotor(s) to the rest speed at the end of each inspiratory phase. Thus, the rotary compressor is stopped, or rotated at a base rotational speed prior to commencement of each inspiratory ventilation phase. Upon commencement of an inspiratory phase, the rotary compressor is accelerated to a greater rotational speed for delivering the desired inspiratory air flow. At the end of the inspiratory phase, the rotational speed of the compressor is decelerated to the base speed, or is stopped, until commencement of the next inspiratory ventilation phase. These prior art systems typically use a programmable controller to control the timing and rotational speed of the compressor.

During operation of the ventilator, it is desirable to precisely control the rapid acceleration, deceleration, and rotational speed of the rotary compressor in order to generate the required inspiratory pressure, flow rate, or volume to the patient. For instance, depending on the size and capacity of the compressors, it may be necessary to precisely control the speed of the motor from zero to approximately twenty thousand revolutions per minute (20,000 RPM) to generate the desired flow rate. Thus, it may be necessary to accelerate the motor from rest to the full rotational speed of 20,000 RPM in a relatively small amount of time (e.g., on the order of milliseconds).

One type of electric motor with desirable mechanical characteristics for portable ventilators is a brushless DC (BLDC) motor. BLDC motors have small form factors and very high reliability resulting from the lack of brushes and reduced frictional components. BLDC motors are reversible motors that synchronize the poles of a rotor with a rotating stator field. Classes of BLDC motors include permanent magnet types and variable reluctance types.

In BLDC motors that use permanent magnets, the rotor is made of magnetic materials that provide high flux, resulting in good torque-to-size ratio at moderate cost. The inherent dynamic braking and low rotor speed of the permanent magnet design ensure smooth operation and provide the type of rapid acceleration needed for the inspiratory cycle of a mechanical ventilator. In addition, BLDC motors have very low torque ripple and are easily controllable over a broad range of speeds.

BLDC motors provide rapid acceleration and deceleration capability, as well as exceptional efficiency under full load conditions. These features are desirable in applications that require performance with minimal power consumption. However, simple BLDC motor controllers (e.g., controllers that rely solely on commutation states for motor control) do not provide the type of precision speed control required in portable ventilator systems. Portable ventilator systems require substantially instantaneous speed detection (e.g., one speed value every two to four milliseconds) to provide the necessary transient response in the speed control loop. Speed detection based on sparse commutation state information would have a strong negative impact on the transient response of the speed control loop, especially at low speeds.

Simple BLDC motor controllers use a small number of commutation states (e.g., six states for a three-phase device) to describe the rotor position at any moment in time. Position information is therefore relatively coarse. For commutation control, this coarse position information is sufficient. For speed control, however, such coarse position information is problematic. The rate at which commutation position information is available is equal to the number of commutation states multiplied by the current speed of the rotor. At higher rotor speeds, there are more commutation position samples (i.e., state changes) per unit time, reducing the total amount of time required to compute an accurate speed value. However, as the rotor speed decreases, the commutation position samples become sparser in time, increasing the amount of time required to compute an accurate speed value. As a result, the speed computations from commutation information provide a transient response that is too slow for portable ventilator applications.

In prior art motor control applications, speed control is commonly assisted through the use of a separate speed transducer, such as an optical encoder, which enhances the density of position information with respect to time. Optical encoders typically take the form of a finely notched or perforated disk attached to the rotor shaft of the BLDC motor, extending outward from the radius of the shaft. As the rotor and disk rotate, a light-emitting device (e.g., a light emitting diode (LED)) casts light through the perforations on the disk for detection by one or more photo sensors positioned on the opposite side of the disk. Lenses are sometimes used to focus and direct the light through multiple concentric tracks of perforations.

Each successive notch or perforation of the disk represents the passage of a known angular distance (e.g., with 1024 notches spaced around the disk, one notch=$2^{-10}$ revolutions). A relatively accurate angular speed value can be determined by timing the interval between successive notches, or by counting the number of notches within a fixed sample period.

FIG. 1 is a block diagram of a three-phase BLDC motor controller with an optical transducer. In this example, three discrete Hall effect sensors located in the stator provide rotor position feedback for commutation control. Each discrete Hall effect sensor provides 180 degrees of position sensing coverage. Speed feedback is provided by an incremental optical transducer (i.e., an optical transducer that detects incremental changes in rotor position without reference to an absolute rotor position).

In FIG. 1, discrete Hall effect sensors 115A-C are located in a circle around the spinning rotor, approximately 120 electrical degrees apart to provide full coverage position feedback of the rotor of BLDC motor 110. The binary outputs of discrete Hall effect sensors 115A, 115B, and 115C are connected to a decoder circuit 120 via communication lines 103A, 103B, and 103C, respectively.

The one-bit output of each Hall effect sensor goes high when the positive pole of a magnet attached to the rotor is aligned within the 180-degree arc centered on the given sensor. Because there are three sensors 120 degrees apart, there are roughly 60 degrees of sensor overlap, where the outputs of two sensors are high at the same time (actual region of overlap may depend on the distance between the sensors). Given the above arrangement of sensors, and representing the combined sensor outputs as a three-bit digital word, the possible three-bit values (i.e., states) assigned to rotor positioning are: (1 0 0), (1 1 0), (0 1 0), (0 1 1), (0 0 1) and (1 0 1). The state transitions occur at intervals of approximately 60 degrees. Decoder 120 extracts the six possible sensor combinations or states and feeds the discrete information to commutation control circuit 150, which generates signals for energizing the appropriate stator coils within the motor.

Commutation control 150 provides a commutation signal to PWM generator 170, which, in turn, uses pulse-width modulated signals to drive three-phase inverter block 180. In periodic pulses, three-phase inverter block 180 sources electrical current to one coil of the stator while sinking current through another coil. Due to the direction of the coil windings and the direction of current flow therein, one coil will attract the rotor while the other coil repels. The rotor is thus pulled (and pushed) in the desired direction.

The duty cycles (i.e., the relative pulse-widths) of the signals from PWM generator 170 determine how long the bursts of drive current last within the stator. By modulating the duty cycle based on the control signal received from control function 160, a higher average drive current (or lower average), and a correspondingly stronger (or weaker) pull over time by the stator coils, may be achieved to implement acceleration and deceleration of the rotor.

FIG. 2 illustrates one example of a three-phase inverter coupled to a stator having three coils 200A-200C. The coil arrangement shown is bipolar in nature, meaning that the coils share a single neutral node (209), such that when one coil is sourcing current, another coil must be sinking current. In this way, one coil will be attracting a first pole of a rotor magnet, and a second coil will be attracting the opposite pole of a rotor magnet and/or repelling the first pole. Unipolar arrangements may also be used, where each coil is driven independently, in only one direction.

In FIG. 2, three-phase inverter 180 is implemented with six transistors (201A-B, 202A-B and 203A-B), represented in this example by FETs (field effect transistors). Though not shown, each FET may have a clamping diode coupled in parallel. FETs 201A, 202A and 203A are shown as P-type transistors, though they may also be implemented with N-type transistors. The source nodes of FETs 201A, 202A and 203A are commonly coupled to positive power supply node 204. Similarly, the source nodes of FETs 201B, 202B and 203B are commonly coupled to ground node or negative power supply node 205. The drain nodes of FETs 201A and 201B are commonly coupled to node 206, which is further coupled to coil 200A. The drain nodes of FETs 202A and 202B are commonly coupled to node 207, which is further coupled to coil 200B. Likewise, the drain nodes of FETs 203A and 203B are commonly coupled to node 208, which is further coupled to coil 200C.

Control signals A1, B1 and C1 are coupled to the gates of FETs 201A, 202A and 203A, respectively, and are responsible for determining when FETs 201A, 202A and 203A will source current to coils 200A, 200B and 200C, respectively. Similarly, control signals A2, B2 and C2 are coupled to the gates of FETs 201B, 202B and 203B, respectively, and are responsible for determining when FETs 201B, 202B and 203B will sink current from coils 200A, 200B and 200C, respectively. The control loop determines the timing of control signals A1, A2, B1, B2, C1 and C2, to pull (and optionally push) the rotor to achieve the desired rotation.

Referring back to FIG. 1, an optical encoder is attached to BLDC motor 110. The optical encoder includes LED 104, disk 105 and photo sensor 106. The signal output of photo sensor 106 is provided to timer 130. Speed calculation circuit 140 computes the rotor speed using information available from timer 130. That information may include, for example, the timed interval between detection of consecutive notches or the number of notches detected within a fixed time interval. The computed speed 102 is then compared with speed command 101 to generate a speed error, which is used within control function 160 to generate the modulation control signal for PWM generator 170. Control function 160 may be implemented with, for example, a PI (proportional-integral) controller or a PID (proportional-integral-derivative) controller.

A disadvantage of optical encoders and other speed transducers is that the extra hardware of the encoder takes up space in the housing of the device and increases the overall weight of the device. Further, optical encoders are expensive. For larger devices, the increased size, weight and cost may not be important factors in the device design. However, in portable ventilator design, it is desirable that each ventilator unit be compact, lightweight, and affordable. Thus, the additional size, weight and cost of separate speed transducers make them undesirable as solutions for speed control in a portable ventilator.

These shortcomings of prior art BLDC control systems hinder the use of separate speed transducers with BLDC motors in mechanical ventilator applications. Thus, it is desirable to provide a BLDC motor control system for portable ventilators having accurate rotor speed information and control at all rotor speeds, without the added cost, size and weight of a separate speed transducer.

SUMMARY OF INVENTION

The invention provides a control system for a BLDC motor. An embodiment of the present invention controls the airflow provided to a patient using a brushless DC (BLDC) motor to drive a Roots blower gas compressor. Coupling a Roots blower compressor with a BLDC motor provides a fully capable compressor in a small, cost-efficient package. Using an embodiment of the present invention, the speed of the BLDC motor, and hence the air flow rate, may be precisely controlled using the outputs of analog Hall effect sensors to calculate angular position and speed for a speed control servo.

In one embodiment of the invention, analog sensors are located within a BLDC motor assembly to provide continuous signals based on the magnetic flux sensed from a magnet attached to the rotor of the motor. Unlike the prior art, sensor signals may be sampled at a sample rate that is independent of the angular speed of the rotor. Speed and position accuracy can therefore be maintained across the full range of rotor speeds.

In one or more embodiments, the sensor signals are processed in a position function to obtain the rotor angular position. In accordance with one embodiment of the invention, one possible position function is the arctangent function. The arctangent function may be computed, for example, using an arithmetic computation, a small angle approximation, a polynomial evaluation approach, a table lookup approach, or a combination of various methods. Once the angular position is calculated, the angular speed may be derived by differentiating the angular position over time.

BRIEF DESCRIPTION OF DRAWINGS

FIG. 7 is a schematic diagram of a pressure control servo in accordance with an embodiment of the present invention.

FIG. 8 is an illustration of a flow-rate control servo in accordance with an embodiment of the present invention.

DETAILED DESCRIPTION

The invention provides a control system for a brushless DC motor that can be used to drive a compressor in a portable mechanical ventilator. In the following description, numerous specific details are set forth to provide a more thorough description of embodiments of the invention. It will be apparent, however, to one skilled in the art, that the invention may be practiced without these specific details. In other instances, well known features have not been described in detail so as not to obscure the invention.

Mechanical ventilators are normally bulky machines used mostly in hospitals to assist patients who cannot breathe on their own. Recent advances in technology have resulted in a generation of portable generators that can be used outside the hospital. The current trend is to reduce the size and power consumption of mechanical ventilators while providing the full capability of full size hospital ventilator units.

Mechanical ventilators create positive intrapulmonary pressure to assist breathing. Positive intrapulmonary pressure is created by delivering gas to the patient's lungs so that positive pressure is created within the alveoli (i.e. the final branches of the respiratory tree that act as the primary gas exchange units of the lung). Thus, a mechanical ventilator is essentially a device that generates a controlled flow of gas into a patient's airways during the inspiratory phase, and allows gas to flow out of the lungs during the exhalation phase. Mechanical ventilators use a gas compressor to generate the required airflow.

The present invention involves the precision speed control of an electric motor that may be used to drive a compressor in a mechanical ventilator. Mechanical ventilators may have various modes of operation, e.g., pressure control and volume control. One common thread amongst most mechanical ventilators is that the desired operating mode is achieved by controlling the gas flow rate produced by the gas compressor.

In one embodiment, the motor is a brushless DC (BLDC) motor driving a Roots blower used as a compressor in a portable mechanical ventilator. The flow rate and pressure provided by the compressor are controlled by the speed of the BLDC motor. Unlike in prior art systems where digital Hall effect sensors are used to provide discrete samples of the rotor position and separate speed transducers are used to provide speed feedback of the BLDC motor, embodiments of the present invention employ analog sensors (e.g., analog Hall effect sensors, anisotropic magneto-resistive (AMR) sensors, etc.) to provide continuous rotor position and speed feedback for closed loop control.

Figure 1:
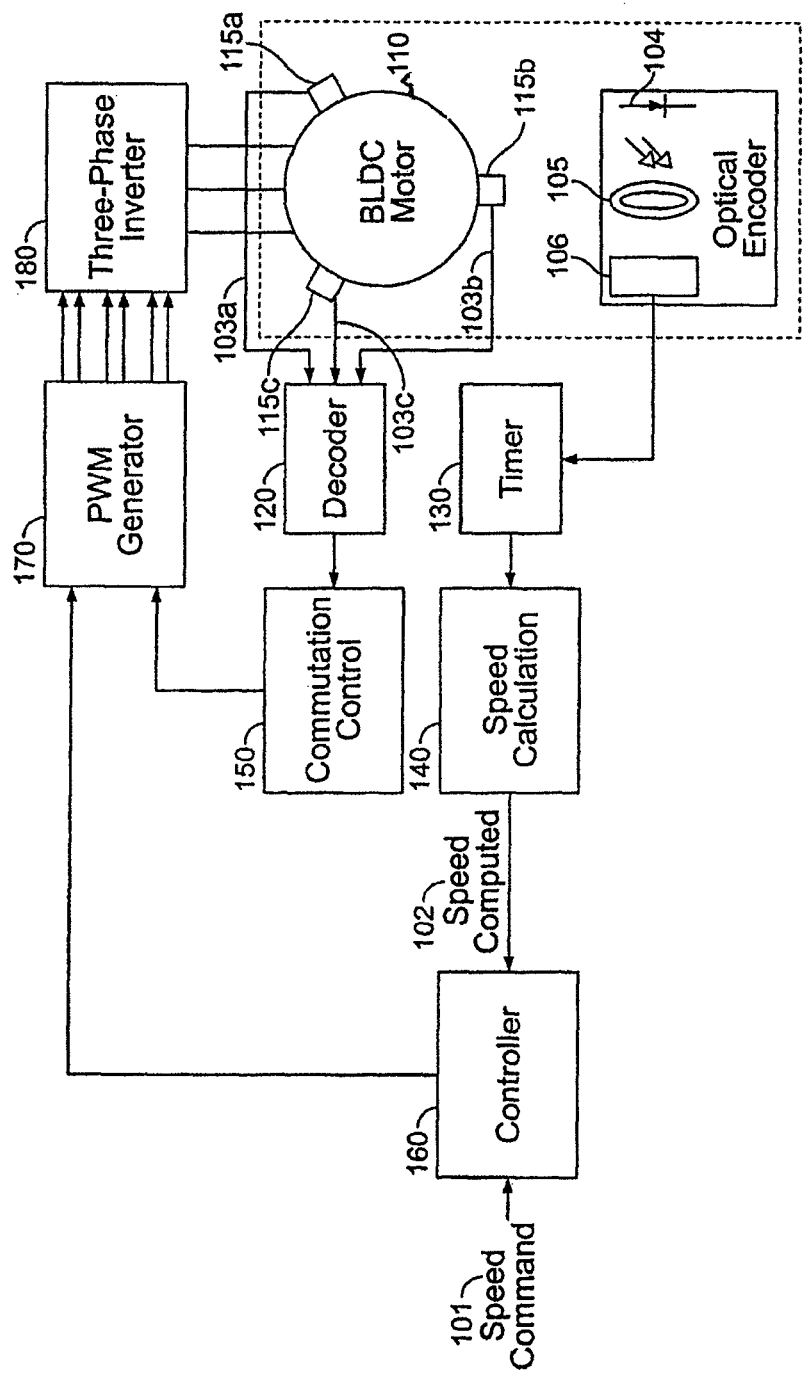
FIG. 1 is a block diagram of a BLDC motor controller with a separate optical encoder.
Figure 2:
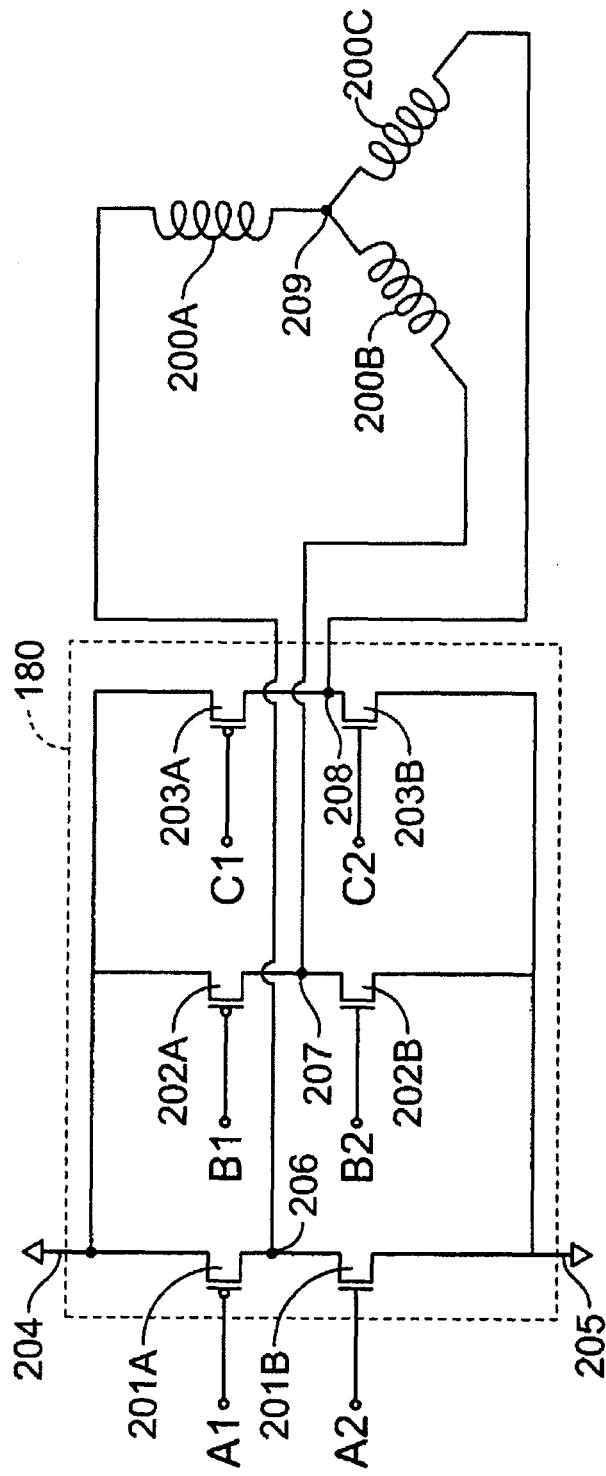
FIG. 2 is a circuit diagram of a three-phase inverter circuit driving a stator with three coils.
Figure 3:
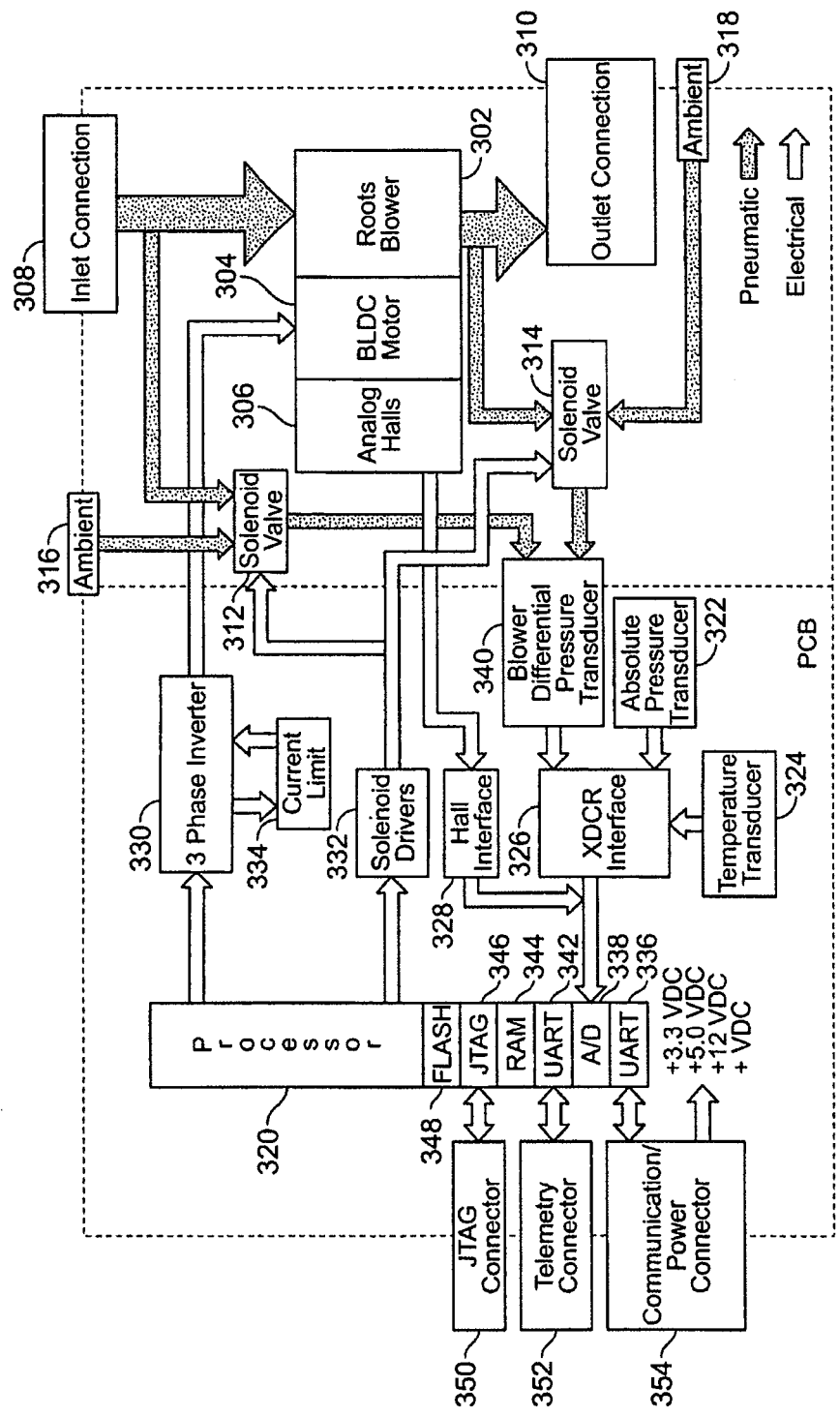
FIG. 3 is a block diagram of a compressor assembly in accordance with an embodiment of the present invention.

FIG. 3 is a block diagram of a motor/compressor system in accordance with an embodiment of the present invention. In this illustration, the motor/compressor system comprises Roots blower 302 coupled to BLDC motor 304. Gas (i.e., air) enters Roots blower 302 via inlet 308. The air from inlet 308 is compressed by Roots blower 302, and then passed to the patient and/or other sections of the mechanical ventilator through outlet 310. Fluid communication paths are provided from the input of Roots blower 302 to solenoid valve 312, and from the output of Roots blower 302 to solenoid valve 314. Ambient air pressure is also channeled to solenoid valves 312 and 314 via ambient inlets 316 and 318, respectively.

The output fluid communication channels of solenoid valves 312 and 314 are provided to blower differential pressure transducer 340 to convert the pressure differential between the two channels into an electrical signal representative of that pressure differential. During normal operation, transducer 340 measures the difference between the output pressure and input pressure of Roots blower 302. By controlling solenoid valves 312 and 314, transducer 340 can also measure the pressure difference between the two ambient pressure inlets during an "auto-zero" phase of transducer 340. Processor 320 provides control of solenoid valves 312 and 314, with solenoid drivers 322 transforming the digital control signals from processor 320 into power DC signals capable of driving the solenoid valves.

Absolute pressure transducer 322 and temperature transducer 324 generate electrical signals representing the absolute pressure level and the temperature. Each of transducers 322, 324 and 340 are coupled to transducer (XDCR) interface block 326, which may provide signal amplification and filtering of the analog signals that are then provided to A/D (analog-to-digital) converter circuit 338. A/D converter 338 transforms the analog signals into digital values that may be processed by processor 320.

In addition to A/D converter circuit 338, Processor 320 also has the following associated circuitry: flash memory 348, JTAG test circuitry 346, random access memory (RAM) 344, and UARTs (universal asynchronous receiver-transmitters) 342 and 336. External JTAG connector 350 is coupled to JTAG circuit 346 to facilitate hardware tests and debugging in accordance with the JTAG standard. Telemetry connector 352 is coupled to UART 342 for the transmission of measured ventilator parameters to a remote system, e.g., for monitoring purposes. Communication and power connector 354 is coupled to UART 336 for facilitating further external communication with the ventilator system, e.g., for operational testing and control. Connector 354 also provides any necessary power signals to the motor/compressor system (e.g., 3.3, 5.0 and/or 15 VDC (volts DC)).

Analog sensors 306 (e.g., analog Hall effect sensors) are arranged on a PC board in a circular pattern perpendicular to the rotor shaft of BLDC motor 304 and adjacent to a two-pole magnet attached to the end of the rotor shaft. Analog sensors 306 provide measurements needed for computation of BLDC rotor position. The analog outputs of sensors 306 are passed through sensor interface 328 (e.g., for amplification and filtering), and then into A/D converter circuit 338, where the analog sensor signals are converted into digital values for processing within processor 320.

Processor 320 executes software instructions to implement certain elements of the motor/compressor control loop, as will be described in detail later in this specification. Processor 320 may be implemented, for example, with a general purpose processor or with a digital signal processor (DSP). Other embodiments may implement the functionality of processor 320 in firmware (e.g., instructions stored in an EPROM) or as equivalent logic in a hardware device (e.g., an ASIC (application specific integrated circuit) or an FPGA (field programmable gate array)).

Processor 320 receives the digitized sensor signals and pressure measurements via A/D converter block 338 (values may use RAM 344 for temporary storage), and determines an appropriate speed control value based upon the control process implemented (e.g., pressure control or volume control). Processor 320 also generates the appropriate commutation control signals given the current commutation state, and modulates the pulse widths of those commutation control signals based on the speed control value. The modulated commutation control signals are provided to three-phase inverter 330.

Three-phase inverter 330 generates drive signals for the individual stator coils in BLDC motor 304, as previously described. The system may also include a current limit circuit 334 coupled to three-phase inverter block 330.

Figure 4:
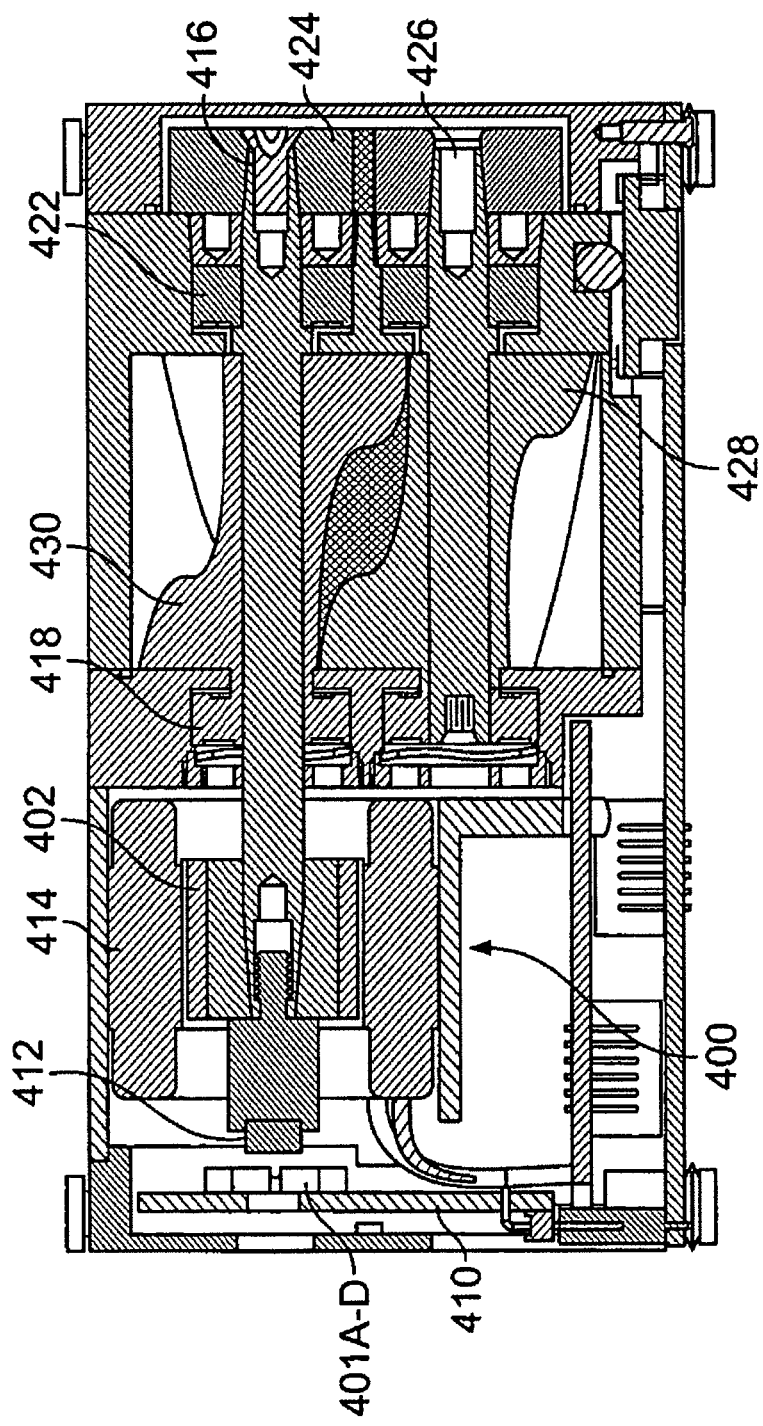
FIG. 4 is an illustration of a cross-sectional view of a motor/compressor system in accordance with an embodiment of the present invention.
Figure 5:
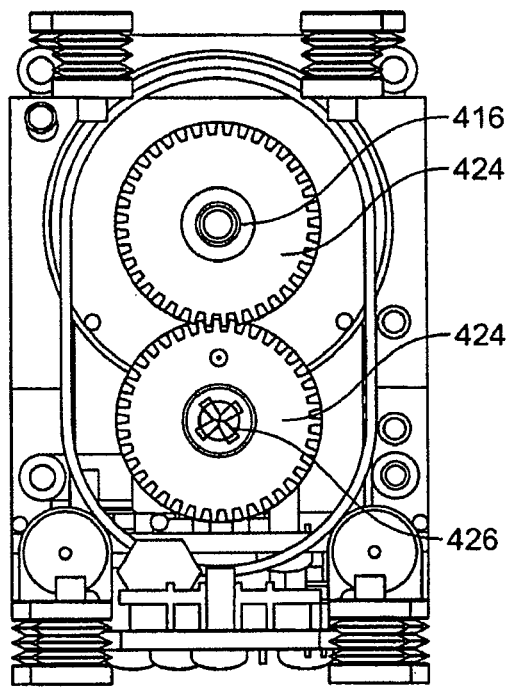
FIG. 5 is an illustration of an arrangement of the drive gears in a Roots blower compressor, in accordance with an embodiment of the present invention.
Figure 6:
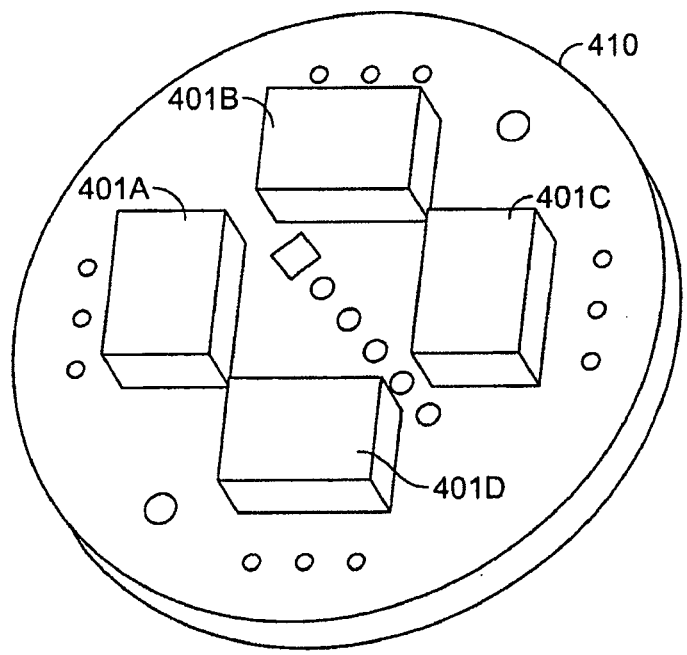
FIG. 6 is an illustration of an arrangement of analog Hall sensors on a PC board in accordance with an embodiment of the present invention.

FIG. 4 is an illustration of a cross-sectional view of a motor/compressor system, in accordance with an embodiment of the present invention. This illustration presents the basic internal components of that motor/compressor system. In this illustration, the BLDC motor (400) end of the motor/compressor system comprises sensor PC board 410, which provides support for a plurality of analog sensors 401A-D (See FIG. 6); rotor shaft 416; rotor 402; magnet 412 attached at the BLDC end of rotor shaft 416; and stator 414. The Roots blower end comprises load bearings 418 and 422, impellers 430 and 428, shafts 416 and 426, and gears 424. The arrangement of gears 424, at the end of rotor shaft 416 opposite BLDC motor 400, is more clearly shown in FIG. 5.

In operation, the BLDC motor controller energizes stator 414 to cause rotor 402 to rotate. The rotation of rotor 402 causes rotor shaft 416 to turn a first impeller 430. Rotor shaft 416 also drives gears 424, which in turn drive shaft 426 and the second impeller 428 of the Roots blower. The operation of impellers 430 and 428 draws air into the Roots blower through a port on one side of the motor/compressor system, and forces the air out a second opposing port at a desired pressure/flow rate. Magnet 412 rotates at one end of shaft 416, eliciting a sensor response from analog sensors 401A-D, which is processed in the servo loops (not shown) of the BLDC motor controller to control the angular speed of rotor 402.

The Roots blower provides the appropriate gas flow rate to achieve positive pressure ventilation (positive intrapulmonary pressure) in a patient. Generally, gas flow produced by a mechanical ventilator either targets a desired volume with variable pressure, or controls the pressure while allowing the volume to vary. In an embodiment of the present invention, each ventilator mode has its own servo loop wrapped around an inner motor speed control loop. The various control modes are discussed below.

Components of the various servo loops described below may be logically implemented within the blower assembly itself (e.g., as software executed by processor 320 or as hardware circuitry), or components may be implemented on an external processor (not shown) that is in communication with the blower assembly. For example, in one embodiment, processor 320 implements the flow rate and speed control servos on PC board 410, while the pressure control logic is implemented by a second ventilator processor that is external to the roots blower assembly, but in communication with processor 320 via a serial link.

Pressure Control Mode

The pressure control mode involves controlling the inspiratory pressure for the duration of the inhalation cycle. In this mode, the Roots blower is required to provide a flow-rate to the patient to achieve a specific waveform or pressure profile. A schematic diagram of the pressure control servo mode is shown in FIG. 7. As illustrated, the desired pressure 701 is compared against the actual pressure 703 developed in the patient's airway to generate an error, which is compensated in block 710 to generate a flow-rate command. The compensation in block 710 may include circuits such as PID controllers (Proportional-Integral-Derivative Controllers) and pressure to flow rate conversion factors.

The flow-rate command is subsequently passed to the flow rate control servo 720, which commands the Roots blower to generate the desired gas flow rate. The flow rate may vary depending on how much gas is needed to satisfy the pressure requirement. The flow rate servo is discussed below.

Volume Control Mode

In the volume control mode, a desired amount of air is delivered to the patient's lungs during the inspiratory cycle. Thus, during inhalation, the ventilator is providing a desired gas flow rate to the patient. FIG. 8 is an illustration of the flow-rate control servo in accordance with an embodiment of the present invention.

As illustrated, the flow-rate command 801 is compared against the actual flow rate 803 in compensation block 810. The actual flow rate 803 may be estimated by using the computed motor speed and measured blower differential pressure 240 in a blower characteristic function 830. Characteristic function 830 may be determined empirically, for example, by observing what the flow rate of the compressor is at known compressor speeds and differential pressures.

The flow-rate error is compensated in block 810 to generate a BLDC motor speed command. The compensation in block 810 may include circuits incorporating any combination of proportional, integral, and derivative controllers (e.g., PI or PID controllers). The speed command is subsequently passed to the speed servo 820, which commands the Roots blower to generate the desired motor speed needed to satisfy the flow requirement.

Speed Control Servo

Figure 9:
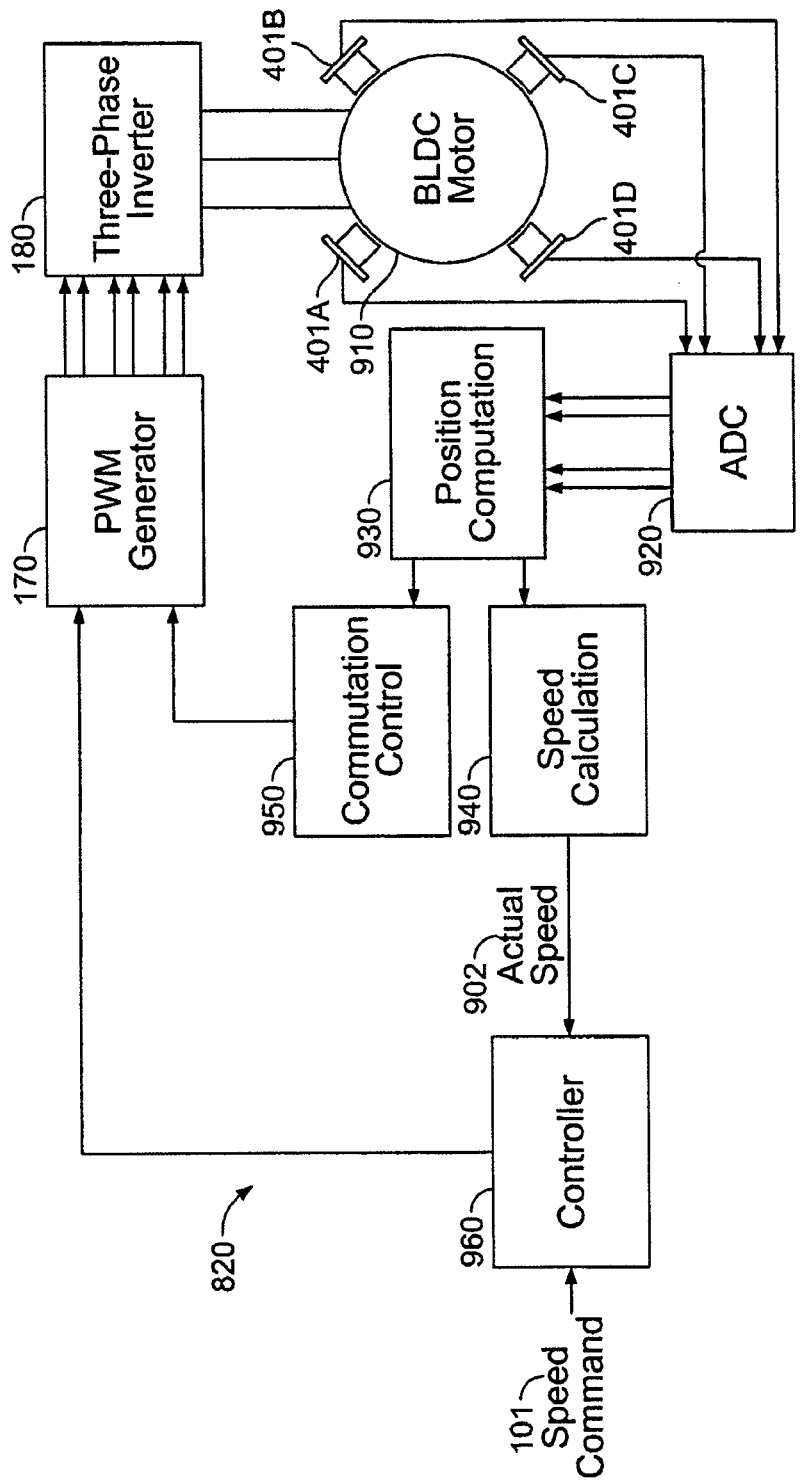
FIG. 9 is an illustration of a speed control servo in accordance with an embodiment of the present invention.

FIG. 9 is an illustration of a speed control servo in accordance with an embodiment of the present invention. In this illustration, the speed control servo comprises controller 960; speed calculation module 940; commutation control circuit 950; position computation module 930; analog-to-digital converter (ADC) circuit 920; pulse-width modulation (PWM) generator circuit 170; three-phase inverter circuit 180; BLDC motor 910; and analog sensors 401A-D.

Controller block 960 compares the desired motor speed (i.e. speed command 101) with the actual motor speed 902 to generate a speed error. The speed error is appropriately compensated and integrated, if necessary, to generate a duty cycle command to PWM generator 170. PWM generator 170 generates modulated control signals, which three-phase inverter 180 uses to drive the stator coils of BLDC motor 910.

Though the commutation circuit is described herein with respect to a three-phase inverter, the present invention may be practiced with any commutation circuit incorporating any number of commutation phases, coils and/or rotor magnets.

The BLDC rotor position is measured using multiple analog sensors (e.g. analog Hall effect sensors or AMR sensors) 401A-D. In one embodiment, the analog sensors produce sine and cosine (quadrature) signals from which the rotor angular position may be derived. The outputs of the analog sensors are converted to digital equivalents in ADC block 920, and the digitized sine and cosine signals are used to compute rotor angular position in position computation block 930. The sample rate of ADC block 920 may be set to any value sufficiently high to provide proper commutation at the highest desired speed. Because the quadrature sensor readings are continuous analog signals, the ADC sample rate may be set independently of the angular speed of the rotor, and the sample rate can remain constant over the entire range of angular speeds. Finally, the computed angular position is used to compute the actual rotor speed in block 940, and used in commutation control block 950 to send commutation control signals to PWM generator 170.

Figure 10A:
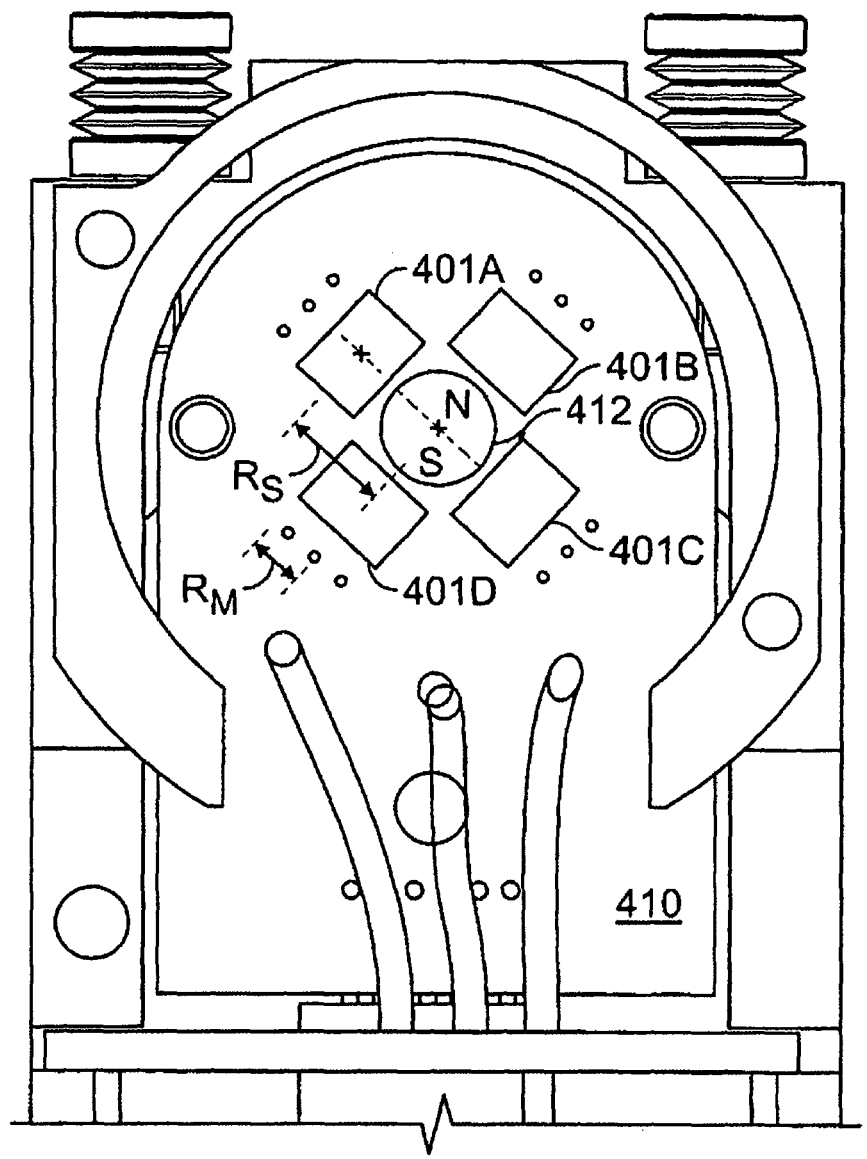
FIGS. 10A and 10B illustrate the positioning of analog Hall sensors with respect to a BLDC rotor magnet to provide rotor position measurement, in accordance with an embodiment of the present invention.

FIG. 10A is plane view of PC board 410 showing the radial positioning of the analog sensors 401A-401D with respect to magnet 412 and the axis formed by rotor shaft 416, in accordance with one embodiment of the invention. Magnet 412 is shown centered on the rotor shaft axis. Magnet 412 may be located at the tip of the BLDC rotor, or at any other location in the BLDC assembly where the sensors can sense the magnetic flux. The radius of Magnet 412 is represented in FIG. 10A by "$R_M$". The four analog sensors are positioned at an equal radial distance "$R_S$" from the central axis of shaft 416, and offset from each other by approximately 90 degrees around that axis. The physical offset of 90 degrees provides for a corresponding phase offset of 90 degrees in the sensor sinusoidal outputs.

Figure 10B:
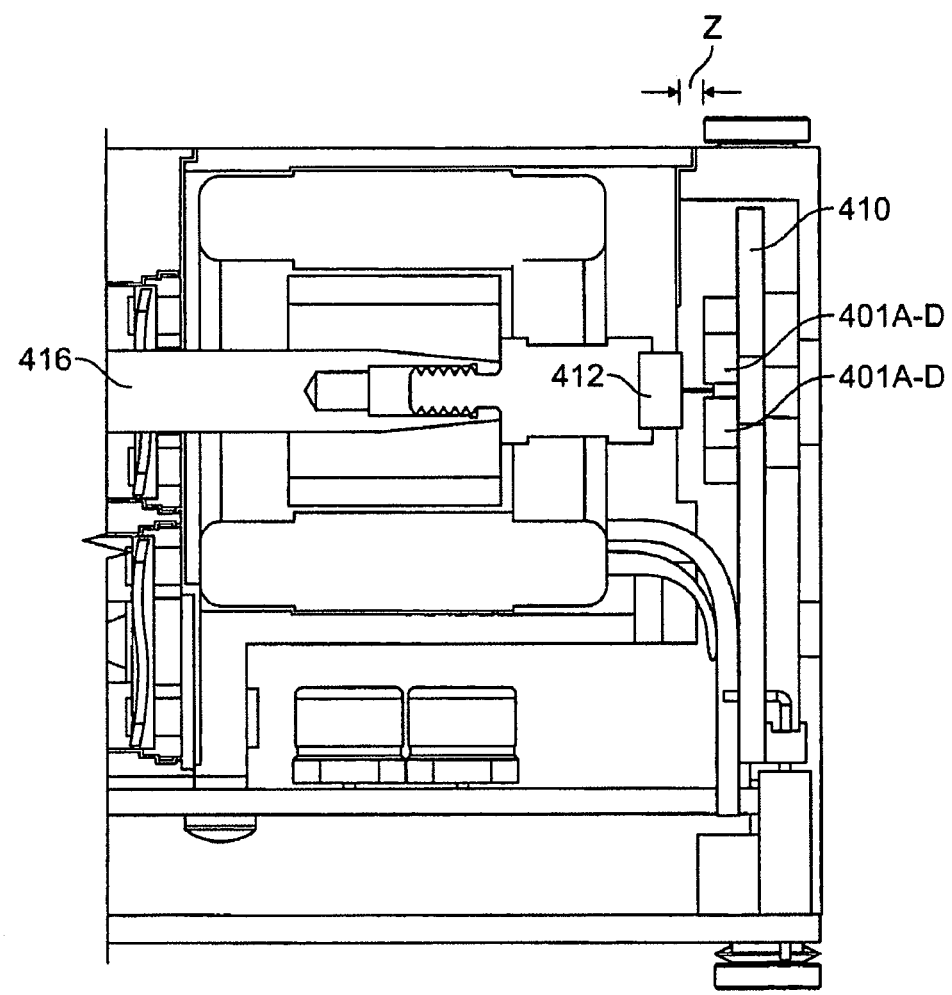

FIG. 10B is a side view of the BLDC motor and control portion of the blower assembly, showing the axial offset between analog sensors 401A-401D and magnet 412. Magnet 412 is shown attached to the end of rotor shaft 416 and analog sensors 401A-401D are attached to PC board 410. The axial offset "Z" from the surface of each analog sensor to the surface of magnet 412 is minimized to prevent weakening of sensor signal strength, while maintaining sufficient distance to avoid any contact or undesired friction effects due to hardware alignment deviations within prescribed design tolerances. In one embodiment, for example, Z is approximately 0.052 inches.

Referring back to the illustration of FIG. 10A, the strength and characteristics of the outputs of the analog sensors depend on the radial distance ($R_S$) of the analog sensor relative to the radius ($R_M$) of magnet 412, or more accurately, the absolute distance between the analog sensor and the surface of magnet 412: $(Z^2+(R_S-R_M)^2)^{0.5}$. Most analog sensors have characteristics such that as $R_S$ approaches $R_M$, the sensor signal strength gets stronger, but the signal quality becomes less ideal in terms of the shape of the output signals (e.g., the signals become more square in nature). The converse is also true, i.e., the shape of the sensor signal improves as $R_S$ increases relative to $R_M$, but the signal strength diminishes. In one or more embodiments, the optimal location may be determined experimentally. In one embodiment, the radial distance $R_S$ may be approximately 0.17 inches, and the radius $R_M$ may be approximately 0.09 inches, for example.

Other embodiments of the invention may use any number of sensors adequate to provide analog position signals that may be used to calculate the rotor angular position. Providing pairs of opposing sensors (i.e., 180 degrees offset), however, and subtracting one opposing sensor's signal from the other can provide performance advantages, such as an improved signal-to-noise ratio. In embodiments where the sensors (or sensor pairs) are offset from each other by a known amount other than 90 degrees, the phase difference may be accounted for in the position calculation.

In the illustration of FIG. 10A, assuming the position of magnet 412 as shown represents zero degrees and the direction of rotation is counter-clockwise, the outputs of sensors 401A and 401C approximate the sine and negative sine, respectively, of the rotor angular position. The outputs of sensors 401B and 401D (being approximately 90 degrees offset from the outputs of sensors 401A and 401C) approximate the cosine and negative cosine of the rotor angular position.

By subtracting the output of sensor 401C from the output of sensor 401A, and subtracting the output of sensor 401D from the output of sensor 401B, sine and cosine signals are obtained with approximately twice the amplitude of each sensor signal alone. Further, minor deviations in the sinusoidal profiles (e.g., due to unequal magnetic strength between the poles of the magnet, or slight misalignment of the magnet with respect to the center of the rotor shaft axis) may be diminished or canceled out by the combination of signals from opposing sensors.

Figure 11A:
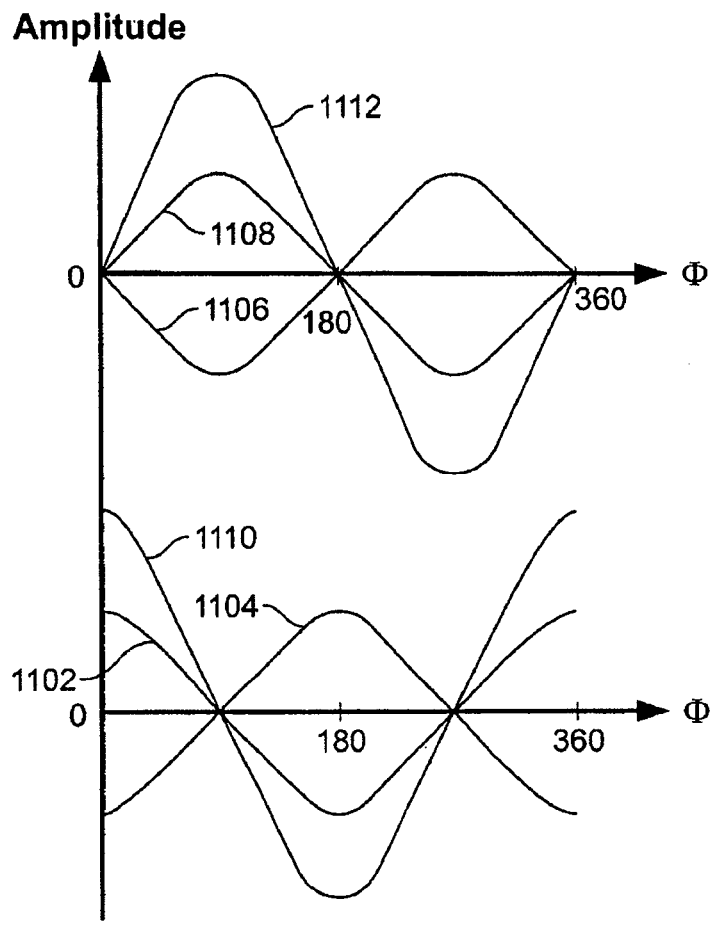
FIGS. 11A and 11B are illustrations of sample analog sensor outputs during BLDC rotor rotation, in accordance with an embodiment of the present invention.

FIG. 11A is an illustration of sample outputs of the four analog sensors of FIG. 10A while the BLDC rotor is rotating. Following the discussion above, signal waveform 1102 represents the output of sensor 401A, and signal waveform 1104 represents the output of sensor 401C. Signal waveform 1108 represents the output of sensor 401B, and signal waveform 1106 represents the output of sensor 401D. If waveform 1104 is subtracted from waveform 1102, the resultant is signal 1110 with characteristics of a sine function and twice the magnitude of either of signals 1104 and 1102. Because the operation is differential, most electrical or common mode noise is eliminated. By the same token, subtracting waveform 1106 from waveform 1108 provides signal 1112 with characteristics of a cosine function and twice the magnitude of either of signals 1106 and 1108.

Figure 11B:
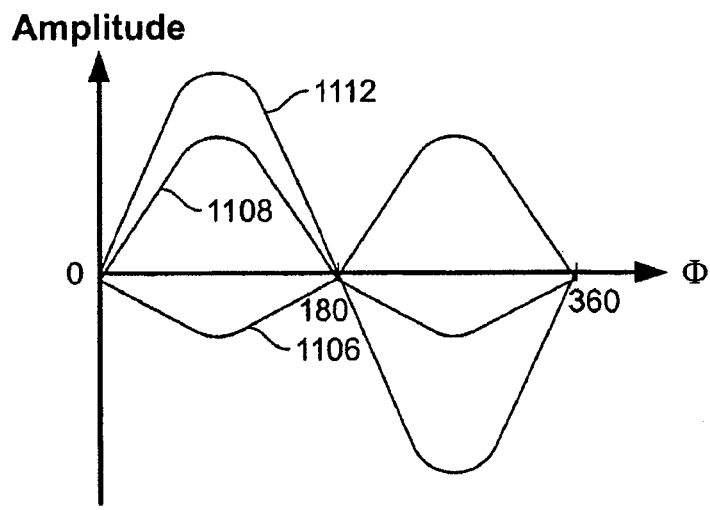

FIG. 11B illustrates how waveforms 1106, 1108 and 1112 are altered under circumstances where magnet 412 is offset from the center of rotor shaft 416 by some small distance, such that the north pole of the magnet rotates closer to the analog sensors than the south pole. As shown, the positive portions of waveforms 1106 and 1108 are boosted by the nearer rotation of the north pole. The negative portions of waveforms 1106 and 1108 are affected in the opposite manner, showing a diminished magnitude. Further, the zero crossings of both waveforms are shifted in position. Use of either sensor signal alone to determine angular position would yield erroneous results. However, as shown by waveform 1112, the subtraction of waveform 1106 from 1108 yields a substantially sinusoidal result, correcting for the magnitude distortion and the zero crossing shifts.

Given the sine and cosine of the rotor angular position, the actual rotor angular position may be obtained using various computational techniques. For instance, in processor 320, the angular position may be generated by computing an angular position function that corresponds to the arctangent of selected quotients of the sine and cosine signals. The arctangent function may be computed using an arithmetic computation, a small angle approximation, a polynomial evaluation approach, a table lookup approach, or a combination of various methods.

The polynomial approach involves generating and storing coefficients for each signal in each quadrant. For instance, the coefficients may be generated in the laboratory by obtaining multiple measurements of the signals for known rotor angular positions in each quadrant, and then using a Least Squares Fit approximation to solve for the coefficients.

Figure 12:
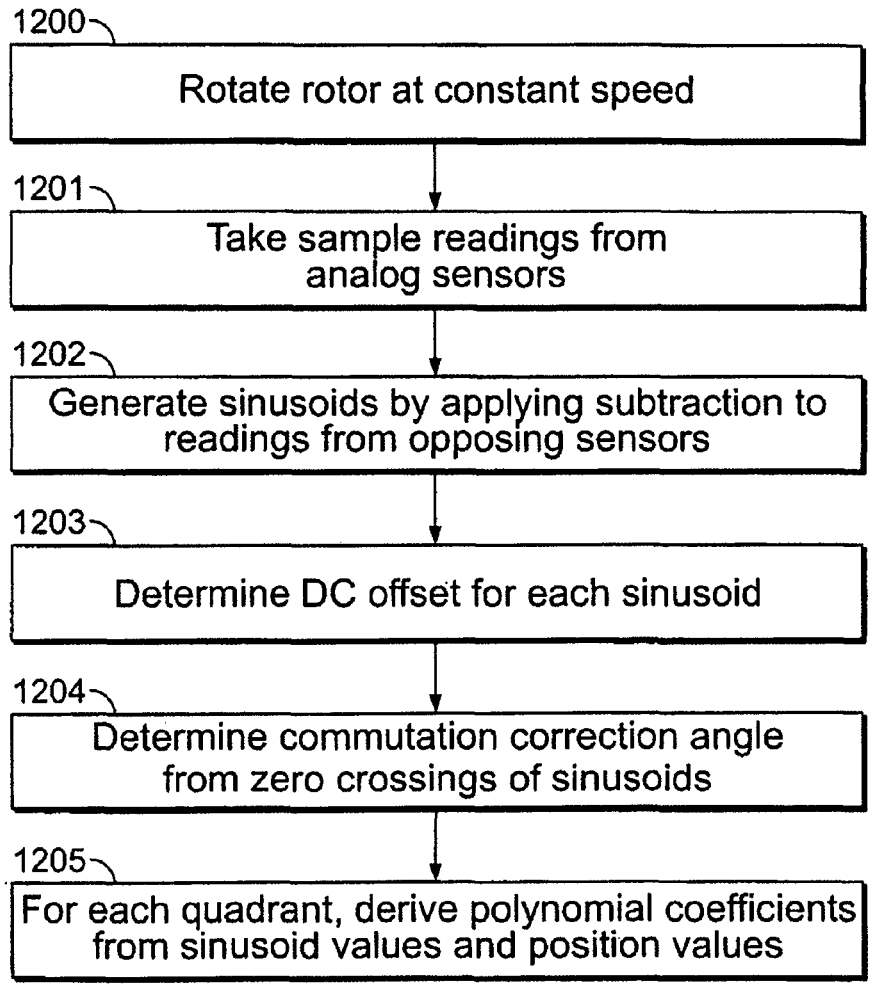
FIG. 12 is a flow diagram of a speed servo calibration process in accordance with an embodiment of the present invention.

For example, coefficient determination may be performed as part of an initial device calibration process, as shown in the flow diagram of FIG. 12. According to one embodiment of such a calibration process, the stator is commutated to achieve a constant angular speed of the rotor in step 1200. This may be done, for example, by using a simple counter to act as the angular position measurement of the rotor. The counter may be accelerated, while the drive current to the stator coils is ramped down from a large initial value to a smaller steady state value. This allows the rotor to synchronize with the stator and stabilize. With the rotor spinning at a constant speed, readings may be obtained from the analog sensors in step 1201. In step 1202, readings from opposing sensors are combined as previously described to provide sinusoidal waveforms 1110 and 1112.

In step 1203, the minimum and maximum values of waveforms 1110 and 1112 may be measured and recorded, preferably but not necessarily over several rotations of the rotor. Those minimum and maximum values may then be used to determine any DC offsets in the sensor values that need to be compensated. Those DC offset values may be used to compensate the calibration sinusoidal waveform data, and may also be stored for use in compensating sensor waveform data during normal operation of the device.

After obtaining DC-compensated readings for the sinusoidal waveforms, in step 1204, the commutation correction angle, that is, the angular offset between the position for the magnet and the simultaneous position of the rotor. In one embodiment, the zero crossings of the sinusoids may be used to identify the commutation correction angle. For example, a zero value from waveform 1110 combined with a positive value from waveform 1112 indicates an angular position of zero degrees for magnet 412. The corresponding commutation angle (determined from the counter) represents the commutation correction angle. This correction angle is needed due to small phase misalignments between the magnet and the rotor that may occur during manufacturing.

In step 1205, sensor readings and the corresponding actual position values from the counter may be used to derive coefficients for each quadrant of rotation. The derived coefficients are stored, indexed by quadrant, for use in computing position values during normal operation.

An example Least Squares Fit approach that may be used to obtain the coefficients is illustrated as follows:

Assuming the following generalized Least Squares Fit equation:

$$L = (H^T H)^{-1} H^T Z$$

Where L is a vector of coefficients (e.g. three coefficients may be adequate if the polynomial equation used to compute the rotor angular position involves three elements: sine, cosine, and a bias), and H and Z are measured sensor and position data, respectively. If L contains three coefficients, then H may be a matrix containing in each row, the sine (s), the cosine (c), and a constant (i.e. one) for each known angular rotor position. Z is a column vector containing each known angular rotor position (p). Thus, the H matrix and the Z vector may be as illustrated below:

$$H = \begin{bmatrix} s_1 & c_1 & 1 \\ s_2 & c_2 & 1 \\ s_3 & c_3 & 1 \\ \vdots & & \\ \vdots & & \\ \vdots & & \\ s_n & c_n & 1 \end{bmatrix}, \quad Z = \begin{bmatrix} p_1 \\ p_2 \\ p_3 \\ \vdots \\ \vdots \\ \vdots \\ p_n \end{bmatrix}$$

The H matrix and Z vector are populated with the measured sensor and position data, and then used to solve the Least Squares Fit equation above. The resulting column vector of coefficients $L=[l_1, l_2, l_3]$ (which may be derived separately for each quadrant or other subset of a rotation) may be applied in the polynomial equation below to obtain rotor angular position (I) from any pair of sensor values. The coefficients $l_1$, $l_2$, and $l_3$ may be stored, indexed by quadrant, in memory, such as the flash memory of processor 320.

$$\Phi = l_1 \sin(\Phi) + l_2 \cos(\Phi) + l_3$$

Where sine($\Phi$) and cosine($\Phi$) are the outputs from the respective sensor pairs. Note that the coefficients may be determined such that the computed rotor angular position overlaps into the adjoining quadrants.

The process of determining the least squares fit may be performed, for example, in processor 320, in a calibration application executing on another processor connected serially to processor 320, or in both processor 320 and in a calibration application executing on another processor (external or internal).

Figure 13:
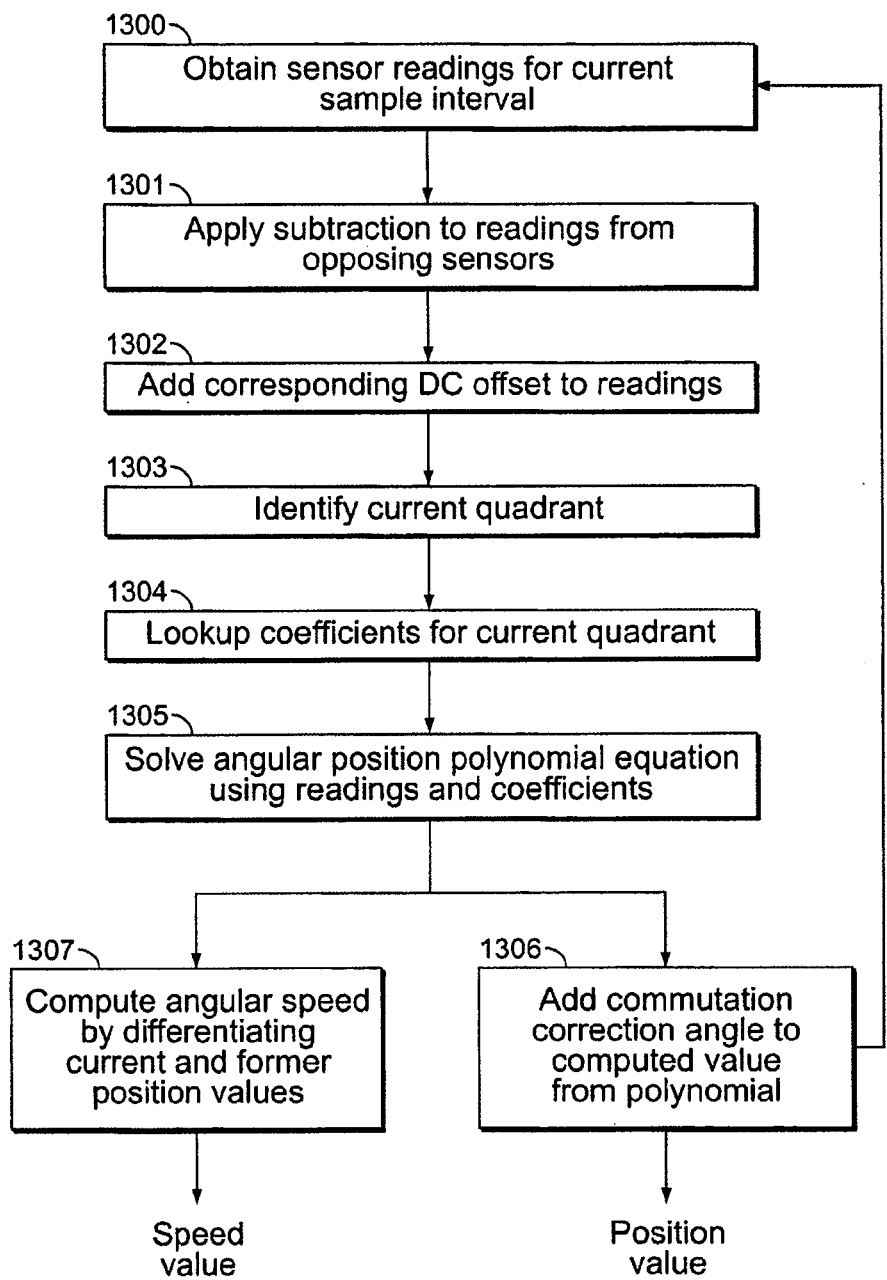
FIG. 13 is a flow diagram of a position and speed computation process in accordance with an embodiment of the invention.

FIG. 13 is a flow diagram of a position and speed computation process used during normal operation, in accordance with an embodiment of the invention. In step 1300, sensor readings are obtained for the current sample interval in accordance with a desired sample rate. In step 1301, those sensor readings are combined as previously described (i.e., by applying subtraction to readings of opposing sensors), and in step 1302, DC correction (determined during the calibration process) may be applied to the combined readings. The current position is derived from the sensor readings by identifying the current quadrant in step 1303, and looking up the appropriate stored coefficients in step 1304. The current quadrant may be easily identified, in one embodiment, by analyzing the signs of the combined sensor readings. For example, when both readings are positive, the current quadrant is the first quadrant (i.e., zero to ninety degrees).

In step 1305, the current coefficients and combined readings are used to solve the angular position equation and yield a computed position value. In step 1306, the commutation correction angle may be added to the computed position value to generate the actual position value for use in commutation control. If, during calibration, the correction angle was applied to the position values prior to deriving the quadrant coefficients, then the correction angle need not be re-applied during normal operation, because the correction angle is already accounted for within the derived coefficients.

The angular speed is computed in step 1307 (which preferably occurs after step 1305 because the commutation correction angle is irrelevant to the speed computation) by taking the derivative of the computed position values, e.g., subtracting the stored position of the prior sample interval from the current position, and multiplying the result by the sampling frequency. Multiplying the position difference by the sampling frequency may be omitted if the speed command from the flow rate servo is normalized appropriately. At the next sample interval, the position and speed computation process begins once more at step 1300.

In another embodiment, a grid of possible angular position assignments to both sensor pair measurements allows implementation of a look-up table for assigning the angular position measurement to the readings of the sensor signals. Thus, a reading may be assigned or dismissed so that the update is omitted if the signals are outside the limits associated with acceptable angular positions.

A table lookup embodiment may automatically assign a predetermined angular position to each pair (sine and cosine) of valid coordinates or skip a position update when either of the sine and cosine data is not to be trusted. Thus, using a table lookup to compute the phase angle allows for elimination of signals that cannot be trusted for accuracy and provides for sparse real-time computation of the quotients and inverse trigonometric functions (arctangent).

In other embodiments, the angular position computation process may be done entirely in the analog domain. In such embodiments, the ADC 920 may not be required to convert the sensor outputs to digital form before computation of the arctangent. The arctangent may be approximated for small angles by the tangent obtained from the analog division of the sine and the cosine signals. Such analog division can be implemented by placing a multiplier in the feedback path of an analog multiplier device.

After obtaining the rotor angular position and speed, the position and speed signals may also be filtered using some form of low-pass filter. For instance, an Infinite-Impulse Response (IIR) filter may be employed. An appropriate bandwidth will depend on the sampling rate of the processor, how much delay is tolerable, and the electrical noise characteristics of the environment of the BLDC motor.

Thus, a control system for a BLDC motor has been described. Particular embodiments described herein are illustrative only and should not limit the present invention thereby. The invention is defined by the claims and their full scope of equivalents.

What is claimed is:

1. A portable ventilator apparatus comprising:
   a compressor disposed within the portable ventilator;
   a brushless direct current (BLDC) motor, said compressor driven by said BLDC motor;
   a plurality of sensors disposed within the portable ventilator that provide a plurality of analog signals, said plurality of analog signals representative of an angular position of said BLDC motor;
   a computation circuit disposed within the portable ventilator and in communication with the plurality of sensors configured to compute said angular position or an angular speed of said BLDC motor from said plurality of analog signals; and
   a speed control servo disposed within the portable ventilator and in communication with said BLDC motor for driving said angular speed of the BLDC motor to a command speed provided to said computation circuit;
   an analog to digital converter directly coupled with said plurality of sensors that directly receives the analog signals provided by said plurality of sensors, and that converts the analog signals to digital signals, and that outputs the digital signals;
   a processor that receives the digital signals, that generates control signals based on the digital signals, and that provides the control signals to a three phase inverter that generates drive signals to control said BLDC motor.

2. The apparatus of claim 1, wherein said BLDC motor includes a plurality of stator coils that receive said drive signals.

3. The apparatus of claim 1, wherein said plurality of sensors includes pressure sensors.

4. A method for controlling a portable ventilator comprising:
   receiving directly one or more analog sensor signals having an amplitude related to an angular position of a rotor of a brushless direct current (BLDC) motor at an analog to digital converter from one or more analog sensors directly coupled with said analog to digital converter;
   converting the analog signals into digital signals via the analog to digital converter;
   processing the digital signals to obtain current information about the speed of the BLDC motor via a processor;
   generating control signals to control the speed of the BLDC motor;

controlling the speed of the BLDC motor with the control signals to drive a compressor of said portable ventilator.

5. The method of claim 4, wherein the BLDC motor drives said compressor to produce a flow-rate to a patient to achieve a specific waveform or pressure profile.

6. The method of claim 4, wherein the BLDC motor drives said compressor to produce a flow-rate to a patient to deliver a specific volume of air.

7. A method for controlling a portable ventilator comprising:
   receiving directly one or more analog sensor signals having an amplitude related to an angular position of a rotor of a brushless direct current (BLDC) motor at an analog to digital converter from one or more analog sensors directly coupled with said analog to digital converter;
   converting the analog signals into digital signals via the analog to digital converter;
   processing the digital signals to obtain current information about the position of the BLDC motor via a processor;
   generating control signals to control the position of the BLDC motor;
   controlling the position of the BLDC motor with the control signals to drive a compressor of said portable ventilator.

8. The method of claim 7, wherein the BLDC motor drives said compressor to produce a flow-rate to a patient to achieve a specific waveform or pressure profile.

9. The method of claim 7, wherein the BLDC motor drives said compressor to produce a flow-rate to a patient to deliver a specific volume of air.

10. A method for controlling a portable ventilator comprising:
    setting a desired peak pressure;
    measuring an actual output pressure;
    receiving directly one or more analog sensor signals having an amplitude related to an angular position of a rotor of a brushless direct current (BLDC) motor at an analog to digital converter from one or more analog sensors directly coupled with said analog to digital converter;
    converting the analog signals into digital signals via the analog to digital converter;
    calculating a difference between the desired peak pressure and the actual output pressure; and
    controlling the speed of a brushless direct current (BLDC) motor to drive a blower of said portable ventilator to output the desired peak pressure;
    wherein controlling the speed includes calculating said angular position of the motor.

11. The method of claim 10, wherein the difference between the desired peak pressure and the actual output pressure is regulated by proportional-integral-derivative controllers.

12. The method of claim 10, wherein the difference between the desired peak pressure and actual output pressure is regulated using pressure to flow rate conversion factors.

13. The method of claim 10, wherein the speed of said BLDC motor controls the flow rate of the output of said blower, which in turn controls the output pressure.

14. A method for controlling a portable ventilator comprising:
    setting a desired flow-rate;
    calculating an actual flow-rate;
    receiving directly one or more analog sensor signals having an amplitude related to an angular position of a rotor of a brushless direct current (BLDC) motor at an analog to digital converter from one or more analog sensors directly coupled with said analog to digital converter;
    converting the analog signals into digital signals via the analog to digital converter;
    calculating a difference between the desired flow-rate and the actual flow-rate;
    controlling the speed of a brushless direct current (BLDG) motor to drive a blower of said portable ventilator to output the desired flow-rate;
    wherein controlling the speed includes calculating said angular position of the motor.

15. The method of claim 14, wherein the actual flow rate is calculated through estimation by using a computed motor speed and a measured blower differential pressure in a blower characteristic function.

16. The method of claim 15, wherein the blower characteristic function is determined empirically.

17. The method of claim 14, wherein the difference between the desired flow-rate and the actual flow rate includes circuitry implementing a proportional controller.

18. The method of claim 14, wherein the difference between the desired flow-rate and the actual flow rate includes circuitry implementing an integral controller.

19. The method of claim 14, wherein the difference between the desired flow-rate and the actual flow rate includes circuitry implementing a derivative controller.

20. The method of claim 14, wherein the difference between the desired flow rate and the actual flow rate includes circuitry implementing proportional-integral-derivative controllers.

21. The method of claim 14, wherein the difference between the desired flow rate and the actual flow rate includes circuitry implementing proportional-integral-derivative controllers with feed forward term.

22. The method of claim 14, wherein the speed of the BLDC motor is controlled by a speed servo.

* * * * *